(12) United States Patent
Monazami et al.

(10) Patent No.: US 11,766,352 B2
(45) Date of Patent: Sep. 26, 2023

(54) WEARABLE HEAT TRANSFER DEVICES AND ASSOCIATED SYSTEMS AND METHODS

(71) Applicant: BLUEXTHERMAL, INC., Cambridge, MA (US)

(72) Inventors: Reza Monazami, Boston, MA (US); Sahar Jahani, Boston, MA (US); Nicholas Keith Anselmo, Yorktown, VA (US); William W. Hunt, Boston, MA (US)

(73) Assignee: BLUEXTHERMAL, INC., Cambridge, MA (US)

( * ) Notice: Subject to any disclaimer, the term of this patent is extended or adjusted under 35 U.S.C. 154(b) by 159 days.

(21) Appl. No.: 17/646,853

(22) Filed: Jan. 3, 2022

(65) Prior Publication Data
US 2022/0265467 A1  Aug. 25, 2022

Related U.S. Application Data

(63) Continuation of application No. 17/183,313, filed on Feb. 23, 2021, now Pat. No. 11,213,422.

(51) Int. Cl.
*A61F 7/00* (2006.01)

(52) U.S. Cl.
CPC ............ *A61F 7/0085* (2013.01); *A61F 7/007* (2013.01); *A61F 2007/003* (2013.01);
(Continued)

(58) Field of Classification Search
CPC ................. A61F 7/0085; A61F 7/007; A61F 2007/0058; A61F 2007/0009;
(Continued)

(56) References Cited

U.S. PATENT DOCUMENTS

2015/0238349 A1* 8/2015 Giuliani .................. A61F 7/007
602/2
2018/0147086 A1  5/2018 Evans et al.
(Continued)

FOREIGN PATENT DOCUMENTS

WO  2013085552 A1  6/2013
WO  WO-2014/001789  *  1/2014
(Continued)

OTHER PUBLICATIONS

PCT International Search Report for PCT Application No. PCT/US2022/070787, dated May 31, 2022, 21 pages.

*Primary Examiner* — Joseph A Stoklosa
*Assistant Examiner* — Adam J Avigan
(74) *Attorney, Agent, or Firm* — Perkins Coie LLP

(57) ABSTRACT

Wearable heat transfer devices and associated systems and methods are disclosed herein. In some embodiments, a representative heat transfer device can comprise (i) thermoelectric components each having a first side and a second side, (ii) a heat transfer system having a heat exchanger and an array of fluid distribution networks, in which individual fluid distribution networks are thermally coupled to the second side of a corresponding one of the thermoelectric components and fluidically coupled to the heat exchanger, and (iii) a flexible support unit coupled to the first sides of the thermoelectric components and extending at least between individual thermoelectric components, wherein the flexible support unit is a heat spreader configured to enhance heat transfer from a target area.

30 Claims, 25 Drawing Sheets

(52) U.S. Cl.
CPC ............... *A61F 2007/0009* (2013.01); *A61F 2007/0035* (2013.01); *A61F 2007/0042* (2013.01); *A61F 2007/0044* (2013.01); *A61F 2007/0058* (2013.01); *A61F 2007/0075* (2013.01)

(58) Field of Classification Search
CPC ........ A61F 2007/003; A61F 2007/0044; A61F 2007/0035; A61F 2007/0075; A61F 2007/0042
See application file for complete search history.

(56) References Cited

U.S. PATENT DOCUMENTS

2020/0155342 A1    5/2020  Schultz
2020/0368062 A1*  11/2020  Baker ..................... A61F 7/007

FOREIGN PATENT DOCUMENTS

| WO | 2014143305 A1 | 9/2014 | |
|---|---|---|---|
| WO | WO-2018225913 A1 * | 12/2018 | ............. A61F 7/007 |
| WO | 2021016399 A1 | 1/2021 | |

* cited by examiner

WEARABLE HEAT TRANSFER DEVICES AND ASSOCIATED SYSTEMS AND METHODS

CROSS-REFERENCE TO RELATED APPLICATIONS

The present application is a continuation of U.S. patent application Ser. No. 17/183,313, filed Feb. 23, 2021, and is related to U.S. patent application Ser. No. 16/936,358, titled THERMAL MANAGEMENT DEVICE AND SYSTEM, filed Jul. 22, 2020, the disclosures of which are incorporated herein by reference in their entireties.

TECHNICAL FIELD

This present disclosure relates to heat transfer devices configured to be worn by a user, and associated systems and methods.

BACKGROUND

Significant heat fluxes are produced in a wide variety of engineering applications, and there is demand for advanced and efficient heat dissipation systems capable of extracting and dissipating these heat fluxes in order to keep temperatures within acceptable operating ranges. Such demand is present within the field of wearable devices that are configured to dissipate heat from a target area, e.g., to aid with pain or swelling of the user wearing the device. However, despite such demand, a significant gap exists between the heat transfer performance desired by industry and the heat transfer performance readily available with current devices and systems. For example, current single- or two-phase systems are necessarily large and heavy to provide an adequate heat flux to treat swelling and post-surgical applications. However, such systems are uncomfortable in a wearable device and are often too large to work with the complex contours of certain anatomical features, including the knee, shoulder, ankle, leg, arm, back, head, neck, and/or elbow regions.

BRIEF DESCRIPTION OF THE DRAWINGS

Features, aspects, and advantages of the presently disclosed technology may be better understood with regard to the following drawings.

Figure 1A:
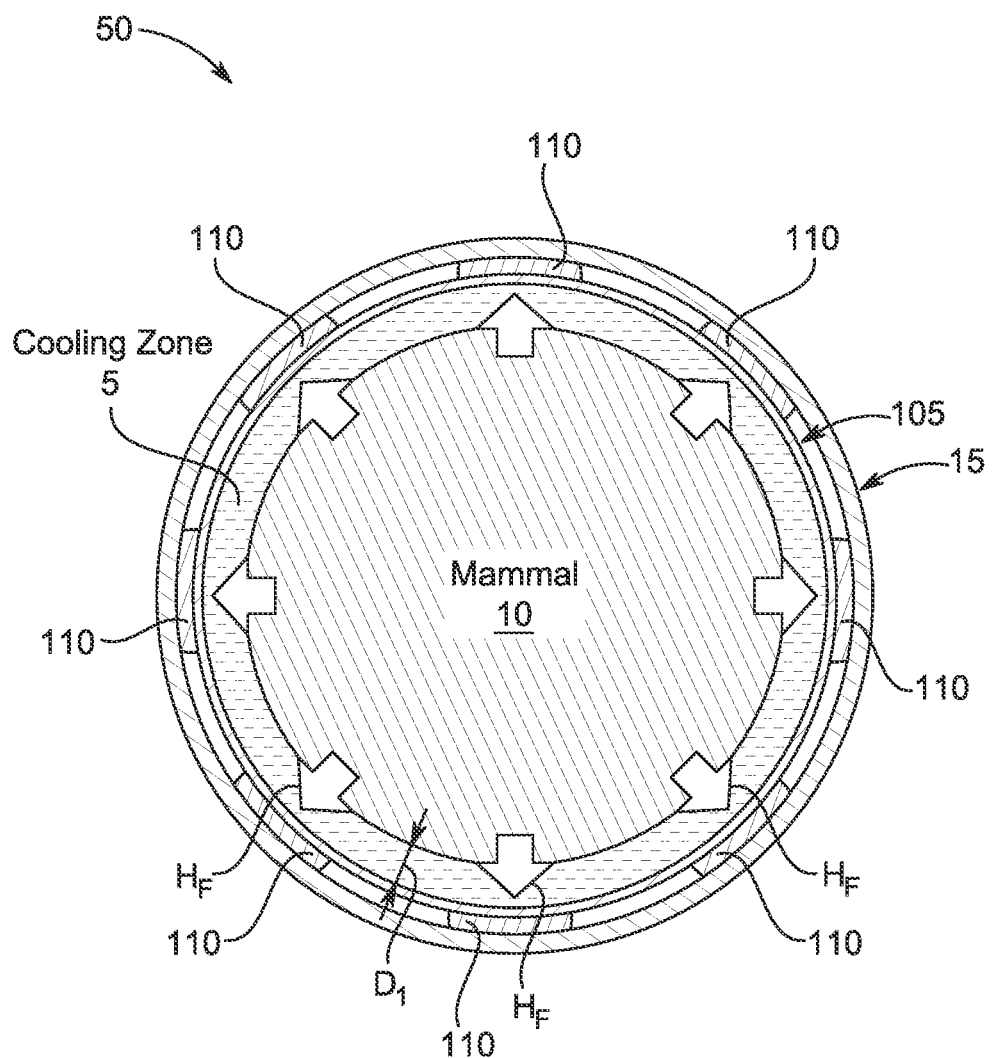
FIGS. 1A and 1B are partially schematic cross-sectional views of heat transfer devices disposed around a portion of a mammal, in accordance with embodiments of the present technology.

A person skilled in the relevant art will understand that the features shown in the drawings are for purposes of illustrations, and variations, including different and/or additional features and arrangements thereof, are possible.

DETAILED DESCRIPTION

I. Overview

Heat transfer devices generally have potential for efficient thermal management of high heat flux operations. For example, two-phase heat transfer devices are able to take advantage of the latent heat of evaporation of a working fluid used within the device that transfers heat and transitions between a vapor phase and a liquid phase. Because the liquid and vapor phases of the working fluid can be kept near a saturation temperature of the working fluid, the two-phase heat transfer devices can enable more effective heat transfer to and/or from the heat source.

However, despite these benefits, the vast potential of phase change heat transfer devices has not been realized. As an example, most such devices rely on heat exchange mechanisms that are limited by the spatial and temporal randomness of boiling. The boiling (or bubbles of vapor) provide significant resistance to the flow of the working fluid and also create dry areas on the heated surface, thus decreasing heat transfer efficiency. Moreover, such devices often encounter "dry-out" of the evaporator and/or overheating damage. Specifically, due to the high resistance to the flow of the working fluid, sufficient liquid is not delivered to the evaporation sites to replenish the evaporated mass, and dry-out and associated overheating damage often ensues.

In addition to the above-noted deficiencies of heat transfer devices generally, current heat transfer devices that can be worn by a user also have limited application. The most prevalent wearable heat transfer devices used to thermally treat a target tissue area, e.g., at low temperatures, are ice bath fluid circulated sleeves and ice/gel packs. For the ice bath sleeves, cold fluid is circulated by a pump through a sleeve wrapped around the target area, and tissue temperature drops as heat is conducted across the sleeve and absorbed by the colder fluid. The heated fluid is then cooled by flowing through an ice bath, and the heat removed from the tissue is absorbed by the ice as it melts. Once the ice in the ice bath melts, the temperature of the bath starts to increase and the circulating fluid gradually warms up. At this point the effectiveness of the system to cool the target tissue area and reduce the pain starts to diminish, and the user or caregiver must empty the bath and add ice and water to reinitiate treatment. The ice/gel packs place similar burdens on the user and caregivers.

Both of these wearable devices have significant shortcomings, including (i) the lack of temperature control at which the tissue is exposed, (ii) a limited time period or capacity for cooling, (iii) an inability to receive continuous cooling therapy without adjusting or tending to the device, and (iv) a lack of flexibility of the device, e.g., due to the pressurized liquid flow and/or rigidness of the icepacks, therein causing an uncomfortable fit for the user. This last shortcoming can further limit the amount of heat transfer between the device and user, as the inflexible nature of the device prevents a conforming fit and/or optimal thermal contact between the device and user. As a result, current wearable devices are unable to adequately thermally treat the target area of a mammal, and are generally ineffective in treating underlying conditions (e.g., pain, swelling, overheating, diminished blood perfusion, diminished nerve connectivity, stroke, etc.).

Embodiments of the present disclosure address at least some of the above described issues by providing a thermal management device and system that, amongst other features, is safer, allows for better temperature control, and enables enhanced thermal contact between the device and the user/mammal, e.g., by being flexible, and lighter and thinner than current related devices. For example, as described in additional detail elsewhere herein, embodiments of the present disclosure can include (i) thermoelectric components thermally coupled to a target area of a mammal, (ii) a heat transfer system or unit thermally coupled to individual ones of the thermoelectric components, and (iii) a flexible support unit coupled to the thermoelectric components and configured to be disposed over and/or around the target area of the mammal. In some embodiments, the flexible support unit is wrapped around a portion of the mammal and fastened to provide a compressive force on that portion, such that the thermoelectric components are arranged to thermally treat the target area. The TECs can each be individually controlled (e.g., set to a particular temperature) by a controller operably coupled thereto. As such, individual regions of the device can be set to different temperatures relative to other regions, and can thus individually treat corresponding target areas of the mammal that the device is disposed on or around. When in a cooling mode, heat can flow to and/or from the target area to the TECs and to the heat transfer system.

As explained in detail below, the heat transfer system can include a fluid distribution network configured to remove heat from the TECs. In some embodiments, the fluid distribution network can include evaporators having chambers that are fluidically coupled to a two-phase closed loop system including a liquid distribution passage and a vapor collection passage. In such embodiments, a working fluid can transition from a liquid phase to a vapor phase within channels of the evaporator chamber and thereby enable relatively efficient heat transfer to occur. In doing so, embodiments of the present disclosure enable the target area of the mammal to undergo, e.g., rapid and controlled cooling and thereby treat certain underlying conditions such as pain, swelling, overheating, diminished blood perfusion, diminished nerve connectivity, and/or stroke, while mitigating damage to the epidermal and/or dermal tissues.

In the Figures, identical reference numbers identify generally similar, and/or identical, elements. Many of the details, dimensions, and other features shown in the Figures are merely illustrative of particular embodiments of the disclosed technology. Accordingly, other embodiments can have other details, dimensions, and features without departing from the spirit or scope of the disclosure. In addition, those of ordinary skill in the art will appreciate that further embodiments of the various disclosed technologies can be practiced without several of the details described below.

II. Heat Transfer Devices and Associated Systems and Methods

FIG. 1A is a partially schematic cross-sectional side view of a heat transfer device 50 ("device 50") disposed around a portion of a mammal 10, in accordance with embodiments of the present technology. As shown in the illustrated embodiment, the device 50 includes (i) a flexible support unit 105 wrapped at least partially around a portion or target area (e.g., skin, tissue, arms, legs, knees, ankles, feet, shoulders, head, neck, face, elbows or any other body part area) of the mammal 10, (ii) a plurality of thermoelectric components or modules 110 ("TECs 110") disposed over the flexible support unit 105 and thermally coupled to the mammal 10, and (iii) a heat transfer system or unit 115 thermally coupled to and configured to remove heat from the TECs 110. As described in additional detail elsewhere herein the heat transfer system 15 can include a single-phase heat transfer system or a two-phase heat transfer system (e.g., evaporative cooling system or pool boiling system). In operation, the TECs 110 can be set to a particular temperature and thus be configured to heat and/or cool the target area of the mammal 10. When the device 50 is in a cooling mode, for example, heat flow ($H_F$) transfers from the mammal 10 to the flexible support unit 105, to the individual TECs 110, and to the heat transfer system 115. As heat is removed from the mammal 10 in such a manner, a cooling zone 15 on the target area forms and can extend to a cooling depth ($D_1$) of the mammal. The depth ($D_1$) can be at least 1 millimeter (mm), 2 mm, 3 mm, 4 mm, or 5 mm, or within a range of 1-5 mm or any incremental range thereof (e.g., 1.5-3 mm). The cooling zone 5 can correspond to a heating zone when the device 50 is in a heating mode. As explained in additional detail elsewhere herein, cooling (or heating) the target area in such a controlled manner can enable the device 50 and other embodiments of the present technology to efficiently thermally treat target areas in ways current conventional heat transfer devices cannot.

Figure 1B:
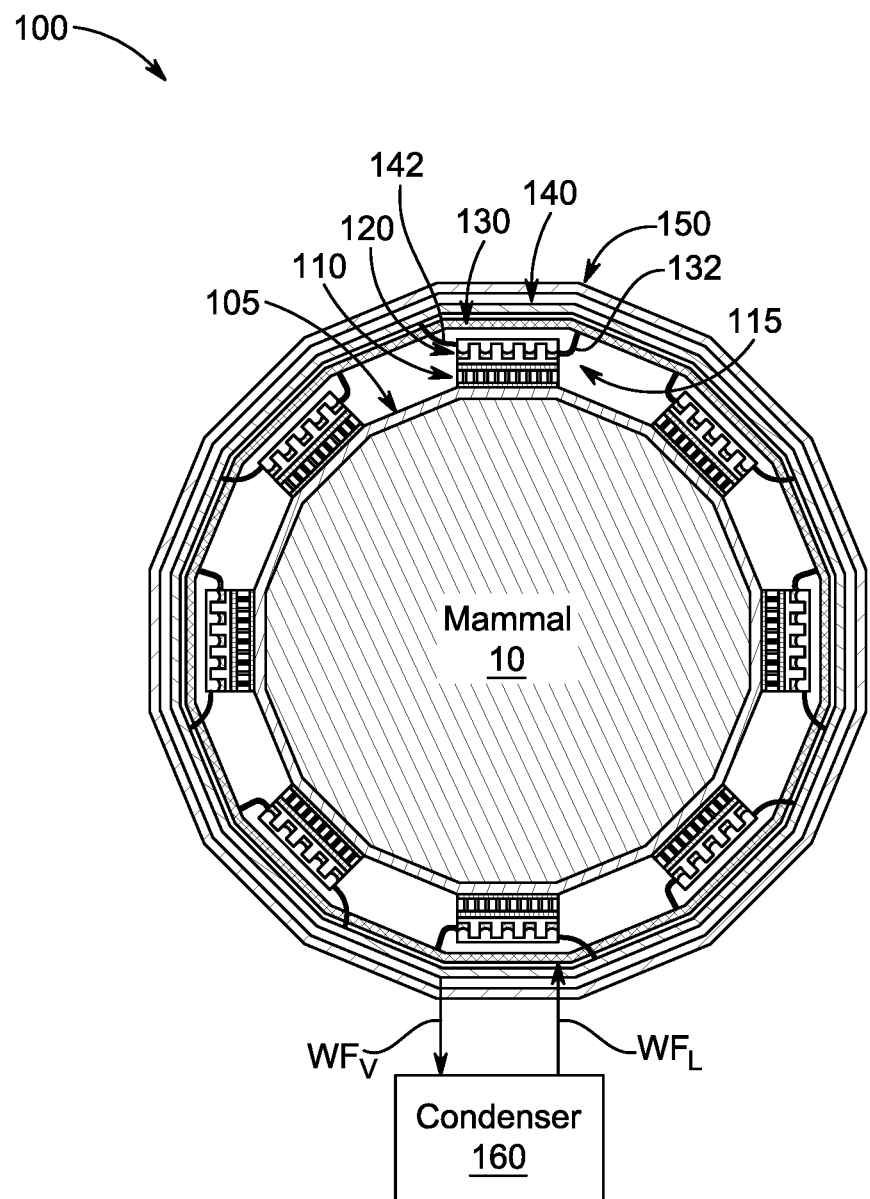

FIG. 1B is a partially schematic cross-sectional view of a heat transfer device 100 ("the device 100") disposed around a portion of a mammal 10. The device 100 can include all or some of the features described with reference to FIG. 1A and the device 50. As shown in FIG. 1B, the heat transfer system 115 is a two-phase heat transfer system and can include an array of fluid distribution networks or evaporators 120 each thermally coupled to a corresponding one of the TECs 110, a liquid distribution passage 130 configured to provide a working fluid in a liquid phase (WF$_L$) to each of the evaporators 120 (e.g., at a respective inlet 132 of each of the evaporators 120), a vapor collection passage 140 configured to receive the working fluid in a vapor phase (WF$_V$) from each of the evaporators 120 (e.g., at a respective outlet 142 of each of the evaporators), and a heat exchanger or condenser 160. The condenser 160 is configured to receive and condense the vapor working fluid (WF$_V$) from the vapor collection passage 140, and provide the condensed liquid working fluid (WF$_L$) to the liquid distribution passage 130. In some embodiments, the condenser 160 is passively air cooled or actively cooled with a cooling fluid provided via one or more pumps. The heat transfer system 115 can comprise a closed loop two-phase system, wherein flow of the working fluid through the heat transfer system 15 is driven by heat transferred from the TECs 110 to the individual evaporators 120. In some embodiments, the heat transfer system can include one or more pumps, and flow of the working fluid through the heat transfer system 115 is driven by the pumps. In other embodiments, flow of the working fluid through the heat transfer system 115 is driven by gravity. For example, when driven by gravity, the condenser 160 may be positioned physically above the other portions (e.g., the evaporators 115) of the heat transfer system 115 such that gravity can provide enough force to circulate the working fluid to the evaporators, where the working fluid is vaporized and returns to the condenser 160 via the vapor collection passage 140. Additionally or alternatively, as explained in more detail elsewhere herein, flow of the working fluid through the heat transfer system can be driven by capillary forces induced by microfeatures (e.g., pillars, pins, or walls) that form channels, present within chambers of the evaporators that drive the liquid phase of the working fluid from inlets of the chambers toward the outlets of the chambers. Additionally or alternatively, in some embodiments the heat transfer system 115 can include a buffer vessel or reservoir configured to hold an excess amount of liquid working fluid (WF$_L$), e.g., to ensure the supply of the liquid working fluid (WF$_L$) can be continuously supplied and does not run. The buffer vessel can be particularly beneficial when the device 100 is operating at more extreme temperatures (e.g., 45° C., −20° C., etc.). In some embodiments the buffer vessel and the condenser 160 may comprise a single integral unit.

As shown in FIG. 1B, the individual evaporators 120 (and corresponding areas of the liquid distribution passage 130 and vapor collection passage 140) can have different orientations. For example, some of the evaporators 120 are disposed substantially parallel to gravitation force, other evaporators are disposed at an angle relative to gravitational force, and yet other evaporators are disposed substantially perpendicular to gravitational force. Accordingly, in some embodiments the heat transfer system 115 can operate despite these different orientations and/or be substantially insensitive to gravitational forces acting on the device 100. That is, the heat transfer system 115 and its individual elements (e.g., the evaporators 120) can operate irrespective of their orientation to gravitational force.

In some embodiments, the heat transfer system 115 can be configured to operate as either a two-phase system, in which the working fluid transitions between liquid and vapor phases, or a single phase system, in which the working fluid remains in a liquid phase that is repeatedly cooled and heated. In some embodiments, the heat transfer system 115 can transition between a two-phase system and a single-phase system, e.g., based on the amount of liquid working fluid supplied. As more liquid working fluid is supplied, the absorptive heat capacity of the circulating working fluid increases and can experience less or no vaporization.

The flexible support unit 105 is thermally coupled to and extends between each of the TECs 110. The flexible support unit 105 can comprise a thermally conductive and/or flexible contact member that acts as a heat spreader to enhance heat transfer to and/or from the target area of the mammal 10 in the regions between the TECs 10. Additionally or alternatively, the flexible support unit 105 can comprise conductive materials and/or biocompatible materials, including metals, metallic alloys, coatings, polymers, silicone, and/or combinations thereof. In some embodiments, the contact member can comprise a metal sheet or material at a first side of the contact member and in contact with the individual TECs 110, and a non-metal sheet or material at a second opposing side of the contact member and in contact with the mammal 10. In some embodiments, the flexible support unit 105 comprises an elastic wrap or material configured to be wrapped around the target area. The elastic wrap can be strapped with a fastener configured to retain the elastic wrap and exert a compressive force against the target area of the mammal 10. As shown in FIG. 1B, the TECs 110 are each disposed over flexible support unit 105, and the flexible support unit 105 is disposed around the mammal 10. In some embodiments, the flexible support unit 105 extends only between individual ones of the TECs 110 and the TECs 110 are disposed directly over the mammal 10 (e.g., in direct contact with the mammal 10). In some embodiments, the flexible support unit 105 can be omitted entirely, and the TEC is disposed over or directly over the mammal 10.

Figure 22:
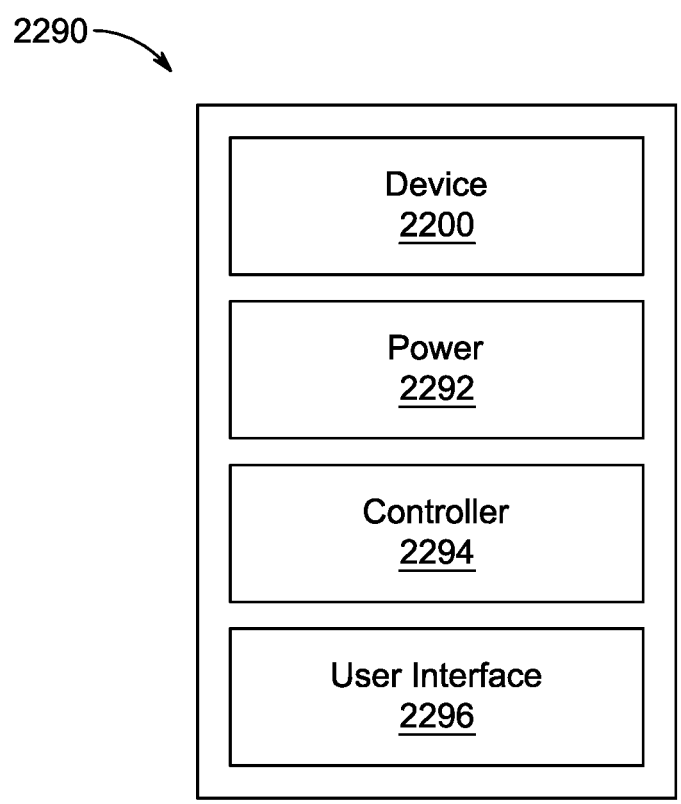
FIG. 22 is a schematic block diagram illustrating a system incorporating a heat transfer device, in accordance with embodiments of the present technology.
Figure 23:
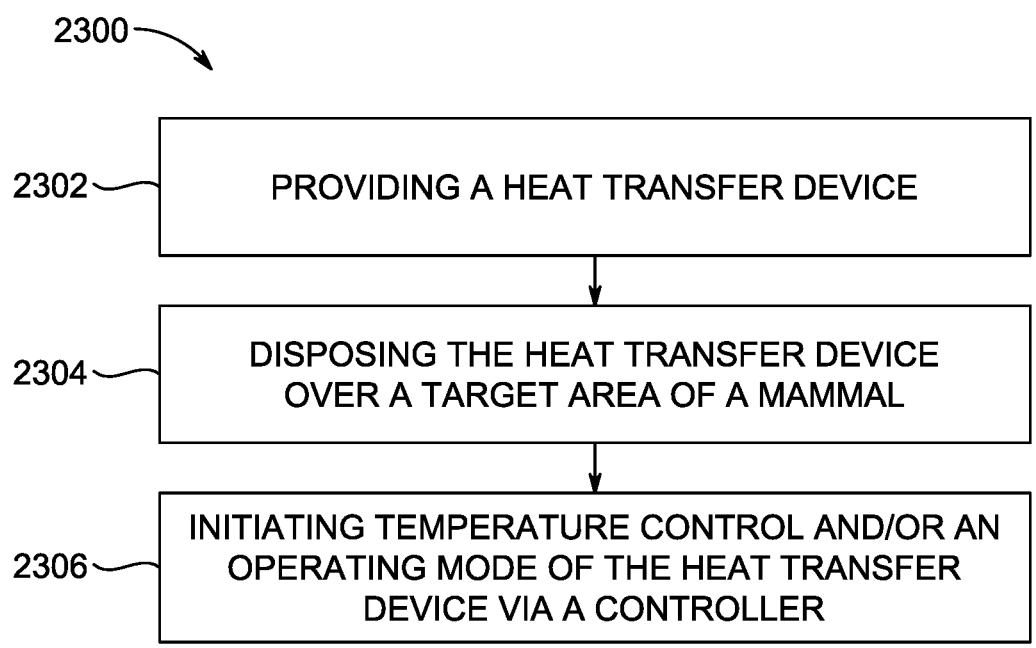
FIG. 23 is a flow diagram illustrating a method for treating a mammal via a heat transfer device, in accordance with embodiments of the present technology.

The TECs 110 can comprise a semiconductor-based electronic component configured to move heat from one side of the TEC 110 to a second opposing side of the TEC 110. The TECs 110 can provide precise, controllable, and/or localized temperature control at the interface between the target area and the device 100. As shown in FIG. 1A, the TECs 110 are thermally coupled to the mammal 10, and can be set to a particular temperature and/or predetermined temperature profile (e.g., constant temperature profile, temperature cycle profile, and/or time based profiles) by a controller (e.g., the controller 2294; FIG. 22) to cool and/or heat the adjacent target area of the mammal 10. Setting the TECs 110, e.g., to a particular temperature can include providing a current to the TECs 110 that corresponds to that temperature. For example, setting a first TEC 110 to a first temperature can include providing a first current to the first TEC 110, and setting a second TEC 110 to a second temperature different than first temperature can include providing a second current different than the first current to the second TEC 110. In doing so, In some embodiments, individual TECs 110 are individually controlled by the controller. For example, the individual TECs 110 can be controlled independent of other individual TECs 110, e.g., to provide localized and variable control when desired. As such, when the device 100 is disposed around a a mammal, different regions of the device 100 can be heated and/or cooled at different temperatures depending on the desired therapy for the individual region. For example, when the device is wrapped around an arm or leg, individual TECs 110 or groups of TECs 110 adjacent a bone region may be set to a first temperature, and other TECs 110 or other groups of TEVs 110 adjacent a more muscular region may be set to a second higher temperature. In doing so, the mammal 10 can experience desired therapy at only certain target areas.

As an example of how the TECs 110 may be operated, in some embodiments the first side of the TECs 110 facing the mammal 10 or the second side of the TECs 110 facing the evaporators 120 can be set to a temperature within a range of 45° C. to −20° C. (e.g., 40° C., 35° C., 20° C., 5° C., 0° C., −5° C., −10° C., −15° C., etc.). In some embodiments, the TECs 110, either alone or in combination with the evaporators 120, can be configured such that the second side of the TECs 110 is set or held at a first temperature or first temperature range and the first side of the TECs 110 are controlled to be cooled from normal surface body surface temperatures to a second temperature or second temperature range. In such embodiments, the second temperature or second temperature range can be more or less (e.g., 5° C., 10° C., 20° C., 30° C., or 40° C. more or less) than the first temperature or first temperature ranges. Additionally or alternatively, upon setting the temperature at the second side of the TEC s 110, the first side of the TECs 110 can be configured to reach a desired temperature within a predetermined time, e.g., no more than 10 seconds, 20 seconds, 30 seconds, 40 seconds, or 60 seconds, or within a range of 10-60 second or any incremental range therebetween. As disclosed elsewhere herein, operation of the TECs 110 may be based on a signal received from one or more sensors configured to detect temperature of the target area, the first side of the TEC 110, or the second side of the TEC.

The TECs 110 can be placed in a heating mode, a cooling mode, or cycle between cooling and heating to control the temperature at the target area. Heat flow across an individual TEC 110 can be a function of temperature difference between its two side and/or the electric power input provide to the individual TEC 110 from a power source (e.g., power 2292; FIG. 22) The mode and/or operation of the mode can be selected based on, e.g., predetermined cycle times and/or temperature sensor feedback. When in the heating mode, the TECs 110 can provide heat to the target area of the mammal 10 (e.g., via the flexible support unit 105) by heating the first side of the TECs 110 which causes the second sides of the TECs 110 to cool. The evaporators 120 can be controlled (e.g., turned off) to mitigate further cooling of the second side of the TECs 110. In some embodiments, the device 100 can further comprise additional resistive heaters that can be controlled via the controller and configured to heat the adjacent target area of the mammal 10.

When in the cooling mode, the evaporators 120 are configured to remove heat from hotter second sides of the TECs 110 and thereby enable the first sides of the TECs 110 to cool the adjacent target area of the mammal 10. As such, in the cooling mode heat flows from the target area of the mammal 10 in a radially outward direction to the TECs 110 and then to the evaporators 120. As previously described, the TECs 110 can also cycle between the cooling and heating modes, which can enhance blood flow and perfusion to the target area. In some embodiments, parameters of the cooling and/or heating modes are based on or limited by safety considerations, such as a maximum heating or cooling temperature and/or maximum amount of heating or cooling time (e.g., 15 minutes, 20 minutes, etc.). Additional details regarding individual TECs 110 are provided elsewhere herein (e.g., with reference to FIGS. 3 and 4).

As shown in the illustrated embodiment, the device 100 includes eight separate TECs 110. In other embodiments, the actual number of TECs 110 may be more or less (e.g., 2, 3, 5, 10, 20, 30, or more) depending on the particular end use of the device 100 and the heating/cooling capacity requirements needed from the device 100. Additionally or alternatively, the TECs 110 may be arranged differently than that shown in FIG. 1. For example, in addition to individual TECs 110 be disposed around a target area (e.g., around a circumference of the mammal 10) as shown in FIG. 1, individual TECs 110 may be stacked on top of one another to increase the heating and/or cooling ability of that particular stack of TECs 110. In such embodiments, a second TEC 110 stacked on top of a first TEC 110 can have one side in contact with the first TEC 110 and another opposing side in contact with the evaporator 120. The stacked arrangement of TECs 110 can be particularly beneficial when more extreme temperatures (e.g., less than 0° C., −10° C., or −20° C.) at the target area of the mammal 10 are desired. This ability to vary the number and arrangement of TECs 110 enables the device 100 to be tailored to a greater variety of end use applications.

As previously described, the evaporators 120 are each disposed over corresponding ones or multiple ones of the TECs 110. The liquid distribution passage 130 and the vapor collection passage 140 are fluidically coupled to each of the evaporators 120, or more particularly to the chambers of the evaporators 120. For example, for an individual evaporator 120 the liquid working fluid ($WF_L$) is supplied from the liquid distribution passage 130 to an inlet 132 (e.g., one of a plurality of inlets) of a chamber of the evaporator 120. As the liquid working fluid ($WF_L$) absorbs heat, it vaporizes to become a vapor working fluid ($WF_V$) and is directed through an outlet 142 (e.g., one of a plurality of outlets) of the chamber of the evaporator 120 to the vapor collection passage 140. The vapor collection passage 140 and the liquid distribution passage 130 are each fluidically connected to the condenser 160 and part of a closed loop system. As such, vapor working fluid ($WF_V$) from the vapor collection passage 140 flows into the condenser 160 at a higher pressure than the liquid working fluid ($WF_L$), and the condensed liquid working fluid ($WF_L$) is thereby driven from the condenser 160 to the liquid collection passage 130 through which it flows to each of the evaporators 120 in a continuous cycle. The condenser 160 is shown schematically in FIG. 1, but in some embodiments can be positioned radially peripheral to each of the liquid distribution passage 130 and vapor collection passage 140 (e.g., the outermost element of the heat transfer system) and radially inward of the insulation member 150. In some embodiments, the condenser 160 can be positioned physically above the evaporators 120 such the condensed liquid working fluid ($WF_L$) provided from the condenser 160 has additional head pressure, which can beneficially provide better circulation of the liquid working fluid ($WF_L$) through the evaporators 120.

The closed loop system illustrated and described with reference to FIG. 1 and elsewhere herein enables embodiments of the present technology to provide the enhanced thermal treatment (e.g., enhanced cooling) relative to the conventional heat transfer devices. Additionally, the closed loop system of embodiments of the present technology mitigates the issues described previously with regard to overheating, dry-out, and the like, as vapor bubbles within the present system are limited and supply of liquid working fluid ($WF_L$) to the evaporators 120 is continuous and readily available by design.

As shown in the illustrated embodiment, the device 100 can further comprise an insulation member or outermost layer 150 peripheral to the heat transfer system, and fully or partially enclosing the other elements of the device 100. The insulation member 150 can prevent or inhibit heat leakage from the device 100 to the ambient environment and/or from the ambient environment to the device 100. Additionally or alternatively, the insulation member 150 can form the outermost element of the device 100. In practice, the insulation member 150 can also serve as a protective barrier between the user (e.g., the mammal 10) and the other elements of the device 100, which can have more extreme temperatures.

In some embodiments, the insulation member 150 can have additional functionality and/or serve other functions. For example, in some embodiments the insulation member 150 can be configured to contain compressed air (or other fluid) with an adjustable pressure to increase and/or decrease the contact pressure applied from the device 100 on the target area of the mammal 110. Altering such pressure can alter blood flow to and/or from the target area, which can be beneficial for treating swelling and/or pain. For example, in some embodiments the device 100 can cool the target area of the mammal 10 for a period of time (e.g., 15-20 minute) at an applied pressure supplied via the insulation member 150 our other member of the device 100, and then cease thermal cooling and decrease the applied pressure for a period of time (e.g., 5-10 minutes). By decreasing the applied pressure, blood flow to the target area is enhanced, while the target area is in a cooled state. Additionally or alternatively, the ability to adjust the applied pressure of the device, and therein the compressive force the device is applying to the target area, can eliminate the need to remove and refasten the device 100.

Figure 2:
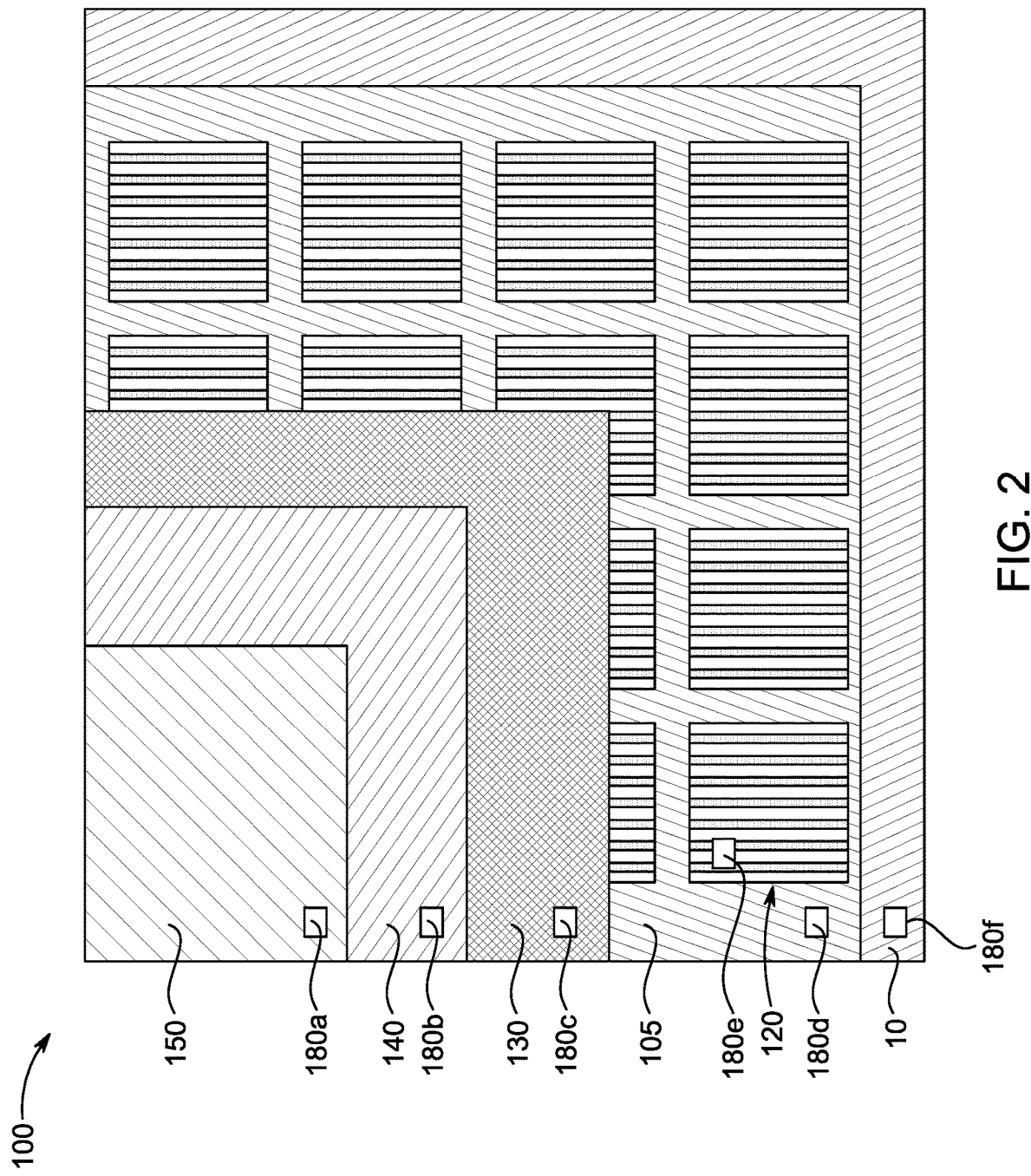
FIG. 2 is partially schematic top view of the heat transfer device of FIG. 1B, in accordance with embodiments of the present technology.

FIG. 2 is top view of the device 100 of FIG. 1, in accordance with embodiments of the present technology. Portions of the elements of the device 100 (as shown in FIG. 1) are removed from FIG. 2 to illustrate a layered arrangement of the elements of the device 100. As shown in FIG. 2, the device 100 includes, in a radially outward direction, the flexible support unit 105, the evaporators 120, the liquid distribution passage 130, the vapor collection passage 140, and the insulation member 150. For illustrative purposes, the condenser 160 (FIG. 1) is not shown in FIG. 2 and the TECs 110 are covered by the evaporators 120.

The device 100 can include one or more sensors 180a-f (collectively referred to as "sensors 180"), which are illustrated schematically. As shown in FIG. 2, the device 100 can include a first sensor 180a on and configured to measure a desired parameter (e.g., temperature, pressure, etc.) of the insulation member 150, a second sensor 180b on and configured to measure a desired parameter of the vapor collection passage 140, a third sensor 180c on and configured to measure a desired parameter of the liquid distribution passage 130, a fourth sensor 180d on and configured to measure a desired parameter of the flexible support unit 105, a fifth sensor 180e on and configured to measure a desired parameter of the evaporators 120, and a sixth sensor 180f on and configured to measure a desired parameter of the mammal 10. Other sensors may also be included depending on the end use of the device 100. For example, one or more other sensors can be on and configured to measure a desired parameter the TECs 110, e.g., to measure individual performance or abnormal operation thereof. Each of the sensors 180 can be in communication with the controller and be used to verify and/or improve safety (e.g., prevent overcooling and/or high pressure zones), efficacy, and operation of the device 100 via the controller.

Figure 3:
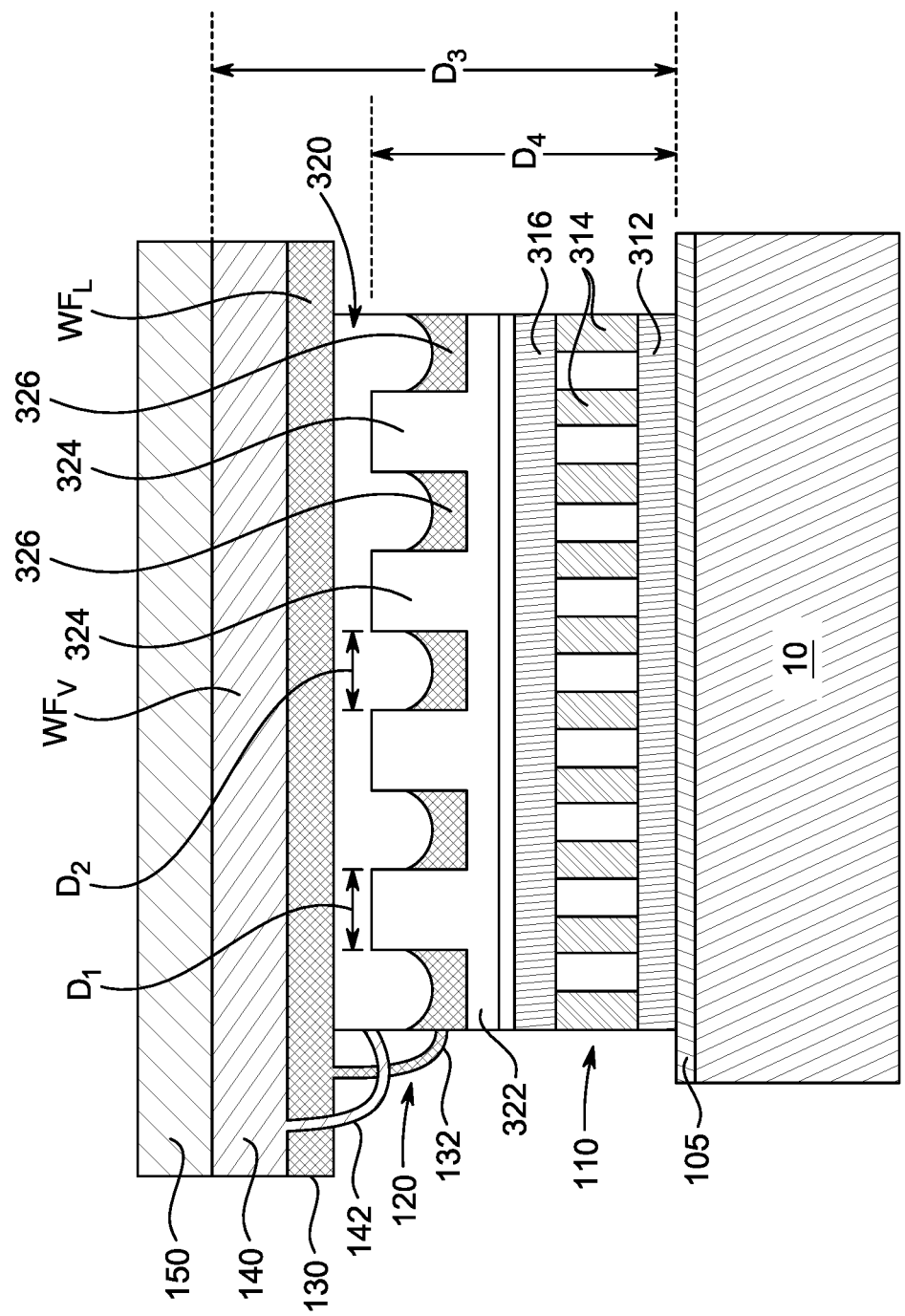
FIG. 3 is a partially schematic enlarged cross-sectional view of a portion of the heat transfer device shown in FIG. 1B, in accordance with embodiments of the present technology.

FIG. 3 is an enlarged cross-sectional view of a portion of the heat transfer device 100 shown in FIGS. 1 and 2, in accordance with embodiments of the present technology. The device 100 shown in FIG. 3 illustrates certain features not viewable in FIG. 1 or 2. For example, as shown in FIG. 3, the TEC 110 of the device 100 includes a thermoelectric first face 312 at a first side of the TEC 110 and adjacent the flexible support unit 105, a thermoelectric second face 316 at a second opposing side of the TEC 110 and adjacent the evaporator 120, and a plurality of thermoelectric legs or pillars 314 extending between the first face 312 and the second face 316. In some embodiments the second face 316 may be omitted and the legs 314 are in direct contact with the evaporator 120. As shown in FIG. 3, the TEC 110 and the heat transfer system including the evaporator 120, liquid distribution passage 130, and vapor collection passage 140 can have a dimension ($D_3$) of no more than 1 mm, 3 mm, 5 mm, 10 mm, 15 mm, 25 mm, or 30 mm, or within a range of 1 millimeter (mm) to 30 mm or any incremental range therebetween, and the TEC 100 and the evaporator 120 can have a dimension ($D_4$) of no more than 1 mm, 3 mm, 5 mm, 10 mm, 15 mm, 25 mm, or 30 mm, or within a range of 1 mm to 30 mm or any incremental range therebetween.

In some embodiments, the TECs 100 (e.g., the first face 312, the second face 316, and/or the legs 314) can comprise a rigid material that is generally inflexible. In such embodiments it can be desirable to limit the footprint of individual TECs 100 to maintain the overall flexibility of the device 100 (or any other heat transfer device disclosed elsewhere herein) and ensure it can conform around or to the geometry of a target area (e.g., the knee). That is, by limiting the footprint of the TECs 100 in such embodiments, and therein the rigid portions of the device 100, the device 100 can have sufficient flexibility, e.g., from the flexible support unit 105 to conform around or to the geometry of a target area to improve thermal contact between the mammal and the TECs 110 of the device 100. In some embodiments, the TECs can have a footprint (e.g., over the flexible support unit 105) of no more than 2 $mm^2$, 3 $mm^2$, 4 $mm^2$, 5 $mm^2$, 6 $mm^2$, 7 $mm^2$, 8 $mm^2$, or 9 $mm^2$, or within a range of 2-9 $mm^2$ or any incremental range therebetween.

In some embodiments, the first face 312, the second face 316, and/or the legs 314 of individual TECs 110 can comprise a flexible material, e.g., to enable the TECs 110 to better conform to a target area when the device is worn by a mammal. Relative to those embodiments in which the TECs 110 are formed of rigid materials, using a flexible material, e.g., for the first face 312 (i.e., the hot side) of the TEC 110 can enable the foot print of the TEC 110s to be larger since the flexibility of the device 100 is no longer limited by the TECs 110. In doing so, the larger heat TECs 110 can enable a higher capacity for heat transfer and/or decrease manufacturing costs for the device 100.

As shown in FIG. 3, the evaporators 120 can include a chamber 320, a base substrate or member 322 within the chamber 320, a plurality of microfeatures 324 that protrude from the base member 322, and channels 326 formed between and defined by adjacent ones of the microfeatures 324. The evaporators 120 can comprise an integral structure (e.g., a single component) and thus include a continuous surface extending along the base member 322 and the channels 326. As shown in FIG. 3, the liquid working fluid ($WF_L$) is disposed within the channels 326 and can form a meniscus, which is due in part to the properties of the liquid working fluid ($WF_L$) and the microfeatures 324, or more particularly the heat of the microfeatures 324 and arrangement (e.g., spacing) of the microfeatures 324 relative to one another. Without being bound by theory, the meniscus can form a thin film portion at an interface with the adjacent microfeature walls that enhances evaporation and thus enables efficient heat transfer from the TECs 110 to the evaporator 120, to the liquid working fluid ($WF_L$), and to the vapor working fluid ($WF_V$). In operation, the heat and/or arrangement of the microfeatures 324 induce capillary forces to the liquid working fluid ($WF_L$) and causes the liquid working fluid ($WF_L$) to move from the inlet region 132 at a first end of the chamber 320 to the outlet region 142 at a second opposing end of the chamber 320 where it exits as a vapor working fluid ($WF_V$). Individual microfeatures 324 can have a lateral dimension ($D_1$) of 5 microns to 250 microns, and can be spaced apart from adjacent microfeatures 324 by a lateral dimension ($D_2$) of 5-1,000 microns.

As shown in the illustrated embodiment, the microfeatures 324 extend from the base member 322 away from the TECs 110. In other embodiments, the evaporator 120 can be disposed in an opposite orientation with the base member 322 being adjacent the liquid distribution passage 130 or insulation member 150 and the microfeatures extending from the base member 322 toward the TECs 110. In such embodiments, the evaporator 120 includes a reservoir adjacent the TEC 110 and containing the liquid working fluid ($WF_L$), and end portions of the microfeatures 324 are submerged within the liquid working fluid ($WF_L$). In operation, the microfeatures 324 induce capillary forces on the liquid working fluid ($WF_L$) and generate vapor working fluid ($WF_V$) that escapes the chamber 320 and collects in the vapor collection passage 140.

Figure 4A:
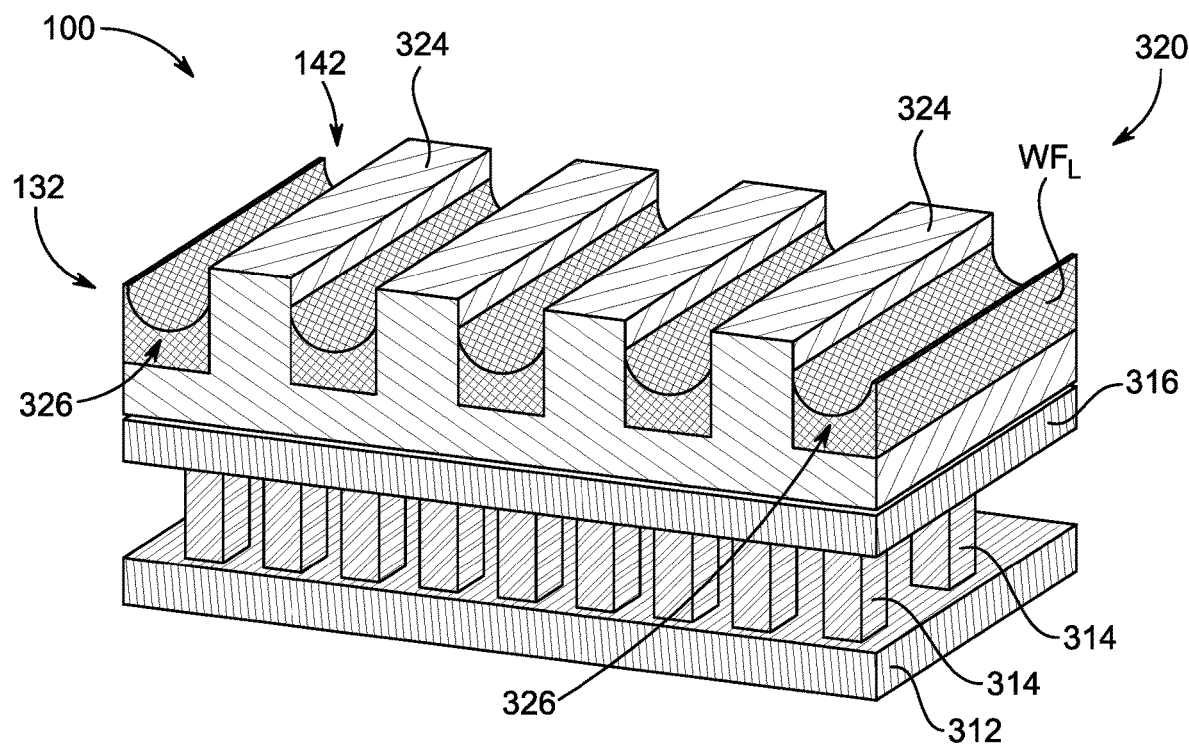
FIGS. 4A and 4B are partially schematic cross-sectional isometric views of a portion of a heat transfer device, in accordance with embodiments of the present technology.
Figure 4B:
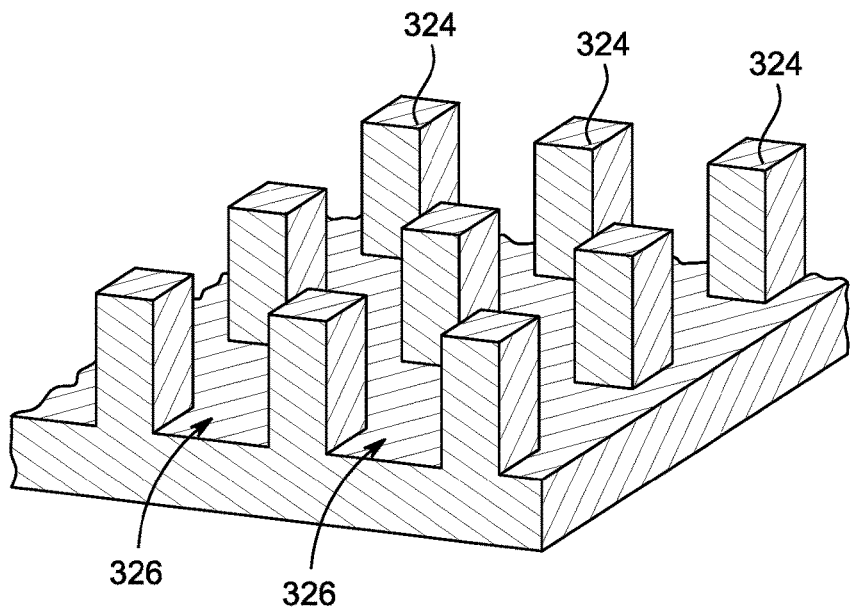

FIG. 4A is a cross-sectional isometric view of a portion of the heat transfer device 100, in accordance with embodiments of the present technology. Only the TEC 110 and evaporator 120 are shown in FIG. 4A and other elements of the device 100 are omitted for illustrative purposes. As shown in FIG. 4A, the evaporator 120 has microfeatures 324 defined by continuous elongated walls that form continuous elongated channels 326 arranged in multiple rows. The channels 326 can be substantially identical to one another and have a uniform width along its length. In some embodiments, the channels 326 can have widths that vary along their length, e.g., becoming narrower as they approach an inlet or outlet of the evaporator chamber. Additionally or alternatively, individual channels may differ (e.g., be wider or narrower) than adjacent channels. Without being bound by theory, such channel design can induce additional favorable pressure gradients on liquid working fluid flow. FIG. 4B is a cross-sectional view of a portion of a heat transfer device 100, in accordance with embodiments of the present technology, in which the microfeatures 324 are pillars or pins arranged in rows and columns, or other suitable arrangements that define channels 326 in the spaces between the microfeatures 326. Although the pin-type microfeatures 324 shown in FIG. 4B have a rectilinear cross-section, they can have circular or other cross-sectional shapes (e.g., hexagonal, octagonal, etc.) As also shown in FIGS. 4A and 4B, the liquid working fluid ($WF_L$) within the channels 326 defined by the microfeatures 324 flows from the inlet region 132 to the outlet region 142 where it exits the chamber 320 as the vapor working fluid ($WF_V$).

Figure 5A:
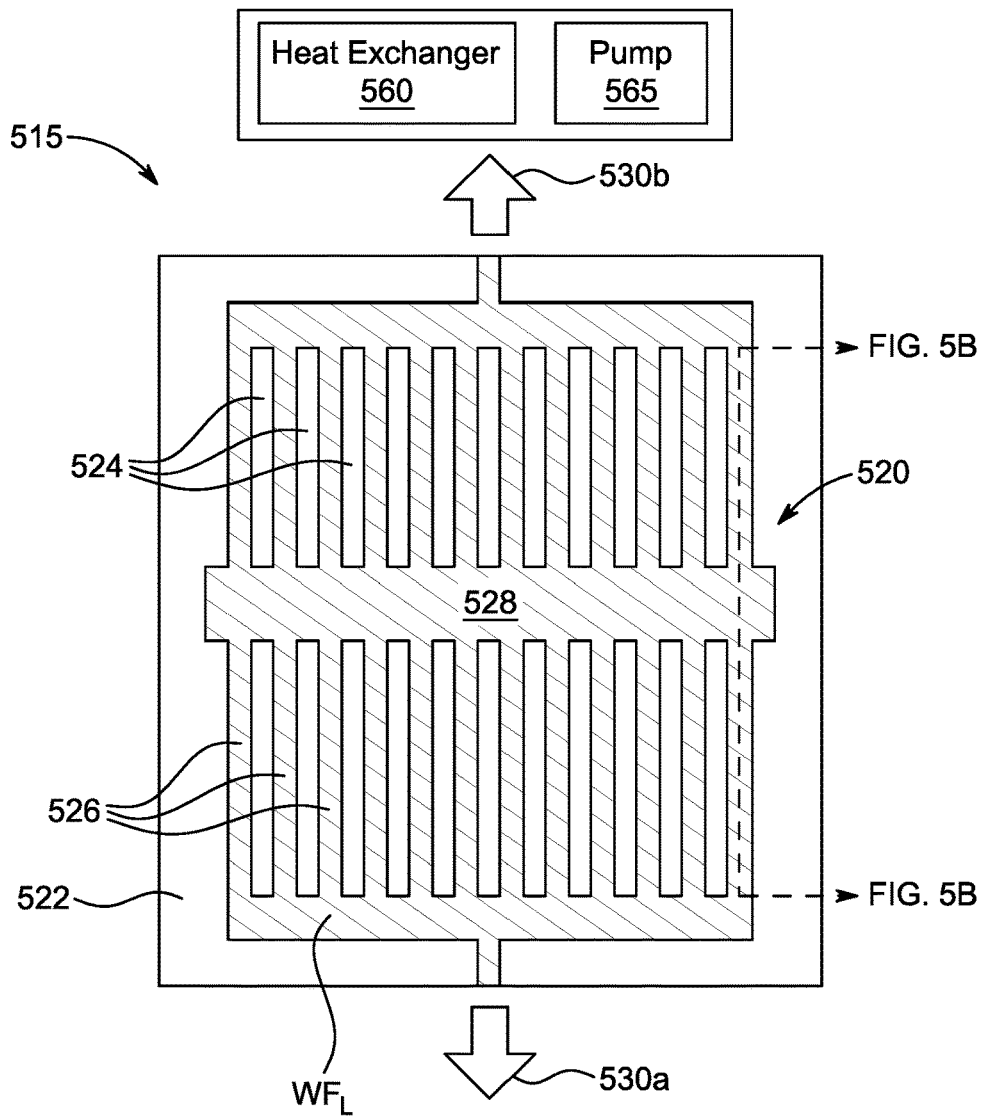
FIG. 5A is a partially schematic top view of a single-phase heat transfer system of a wearable heat transfer device, in accordance with embodiments of the present technology.
Figure 5B:
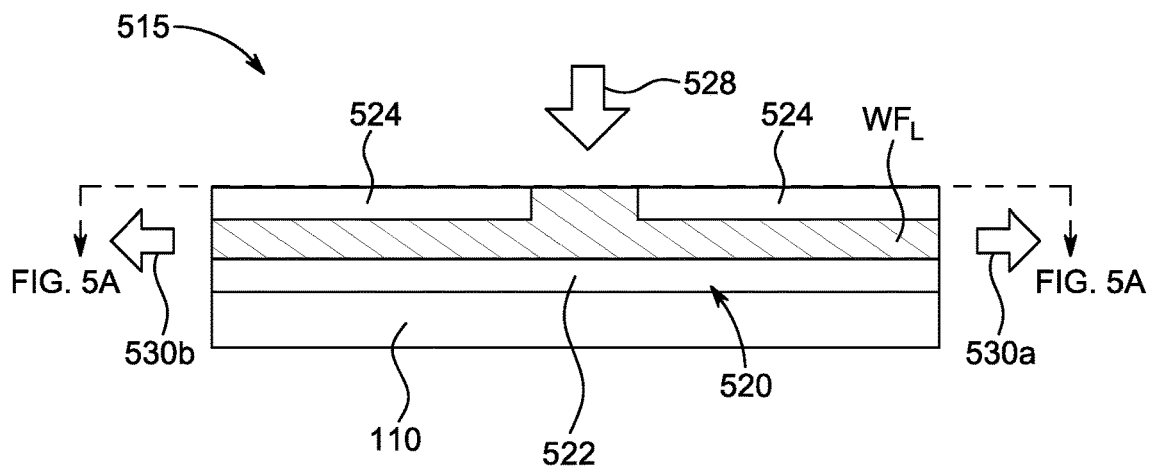
FIG. 5B is a partially schematic cross-sectional side view of the heat transfer system of FIG. 5A.

FIG. 5A is a partially schematic top view of a single-phase heat transfer system 515 of a wearable heat transfer device (e.g., the device 50; FIG. 1A), and FIG. 5B is a partially schematic cross-sectional side view of the heat transfer system 515 of FIG. 5A. Similar to the heat transfer systems or portions thereof previously described (e.g., with reference to FIGS. 1A-4B), the heat transfer system 515 is disposed over the TECs 110 and configured to remove heat therefrom. Referring to FIGS. 5A and 5B together, the heat transfer system 515 can include a base member or substrate 522 disposed over one or more TECs 110. The substrate 522 can include a plurality of microfeatures 524 (e.g., pins or other structures configured to increase and exposed surface area of the substrate) that at least partially define channels 526 of a fluid distribution network or manifold 525. The microfeatures 524 and channels 526 can include the features and/or functionality of the respective microfeatures 322 and channels 324 described elsewhere herein. The channels 524 are configured to receive a liquid working fluid ($WF_L$) to absorb heat from the substrate 522 and/or microfeatures 522. The liquid working fluid ($WF_L$) can be provided to the individual fluid distribution networks 525 at a first temperature and an inlet 528 positioned at an intermediate or central region thereof, and exit the fluid distribution network at a second temperature lower than the first temperature and at outlets 530a-b (collectively referred to as "the peripheral regions 530") at peripheral regions on opposing sides of the fluid distribution network 525. By providing the liquid working fluid ($WF_L$) at an intermediate region, the fluid distribution network 525 can provide more uniform cooling, relative to a fluid distribution network that supplied the liquid working fluid ($WF_L$) on a first side and removed heated the liquid working fluid ($WF_L$) from a second opposing side. As shown in FIGS. 5A and 5B, the fluid distribution network 525 includes only one inlet and one outlet 530a, 530b on each side of the fluid distribution network 525. In other embodiments, the fluid distribution network 525 can include multiple inlets and/or multiple outlets.

The heat transfer system 515 can further include (i) a heat exchanger 560 that cools the heated liquid working fluid ($WF_L$), e.g., to the first temperature, and (ii) one or more pumps 565 configured to circulate the liquid working fluid ($WF_L$) throughout the heat transfer system 515. The heat exchanger 560 can include features and functionality identical to the heat exchanger 160 described elsewhere herein.

Figure 6A:
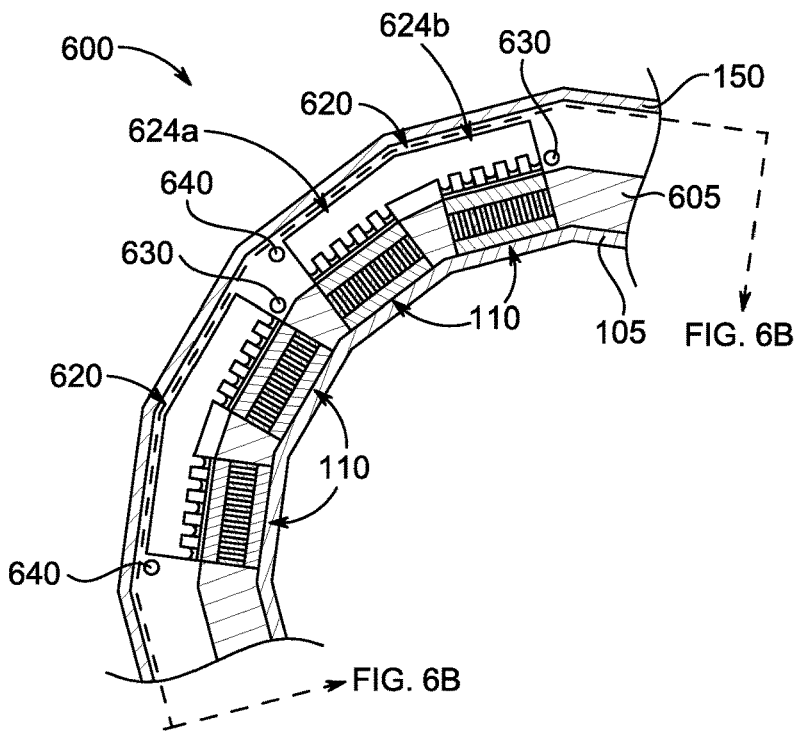
FIG. 6A is a partially schematic cross-sectional view of a wearable heat transfer device, in accordance with embodiments of the present technology.
Figure 6B:
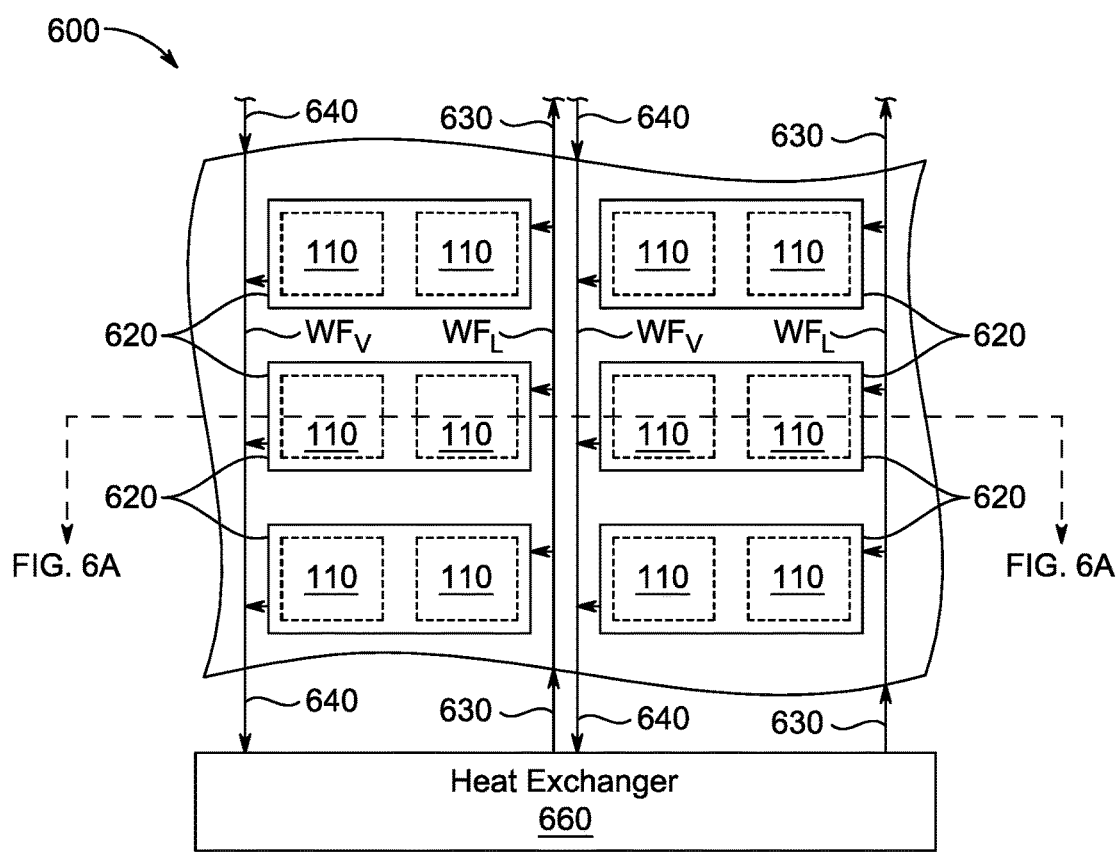
FIG. 6B is a partially schematic top view of the heat transfer device of FIG. 6A.

FIG. 6A is a cross-sectional view of a wearable heat transfer device 600 ("device 600"), and FIG. 6B is a top view of the device 600, in accordance with embodiments of the present technology. The device 600 can be similar to the device 100 previously described in that the device 600 is configured to be worn and wrapped at least partially around a portion or target area of a mammal. Referring to FIGS. 6A and 6B together, the device 600 includes the flexible support unit 105, the TECs 110 disposed over and thermally coupled to the flexible support unit 105, and a heat transfer system thermally coupled to the TECs 110. The heat transfer system of the device 600 includes a fluid distribution network 620 (e.g., an evaporator) having a first array of microfeatures 624a over and thermally coupled to one of the TECs 110, and a second array of microfeatures 624b over and thermally coupled to another one of the TECs 110. The first and second arrays of microfeatures 624a and 624b of each fluid distribution network 620 can be in a common chamber. The arrays of microfeatures 624a-b can be generally identical to the microfeatures 324 (FIGS. 3 and 4) or microfeatures 524 (FIGS. 5A and 5B) shown and previously described.

The heat transfer system of FIGS. 6A and 6B also includes a working fluid inlet passage 630 to provide a cooling fluid to the fluid distribution networks 620 and a working fluid outlet passage 640 to collect a heated fluid from the fluid distribution networks 620. For those embodiments in which the fluid distribution networks 620 include evaporators, the working fluid inlet passage 630 can be a liquid distribution passage configured to provide the liquid working fluid to an inlet region of the evaporator, and the working fluid outlet passage 640 can comprise a vapor collection passage configured to collect the vapor working fluid ($WF_V$) from an outlet region of the evaporator. The working fluid inlet passage 630 and the working fluid inlet passage 640 can be positioned laterally peripheral to the fluid distribution networks 620. As shown in FIG. 6B, the working fluid inlet passage 630 and the working fluid inlet passage 640 can be fluidically coupled to a heat exchanger 660 (e.g., the condenser 160 or heat exchanger 560) configured to (i) receive and cool the heated working fluid from the working fluid outlet passage 640 and supply the cooled working fluid to the working fluid inlet passage 630. As shown in FIG. 6A, the device 600 can further comprise the insulation member 150, positioned radially outward of the fluid distribution network 620 and fully or partially enclosing the other elements of the device 600.

As shown in FIG. 6A, the device 600 can further comprise a flexible backing or matrix material 605 disposed between the fluid distribution networks 620 and the flexible support unit 105, and at least partially surrounding the TECs 110. Stated differently, the TECs 110 are embedded within the flexible matrix 605. The flexible matrix 605 can comprise an elastic material and/or have a flexibility similar to that of the flexible support unit 105. In some embodiments, the flexible matrix 605 can comprise a non-conductive, insulative material such as a foam, gel, or composite, and/or an expandable material. In some embodiments, the flexible matrix 605 can provide additional structural support to the device 600 when worn by a user.

Figure 7:
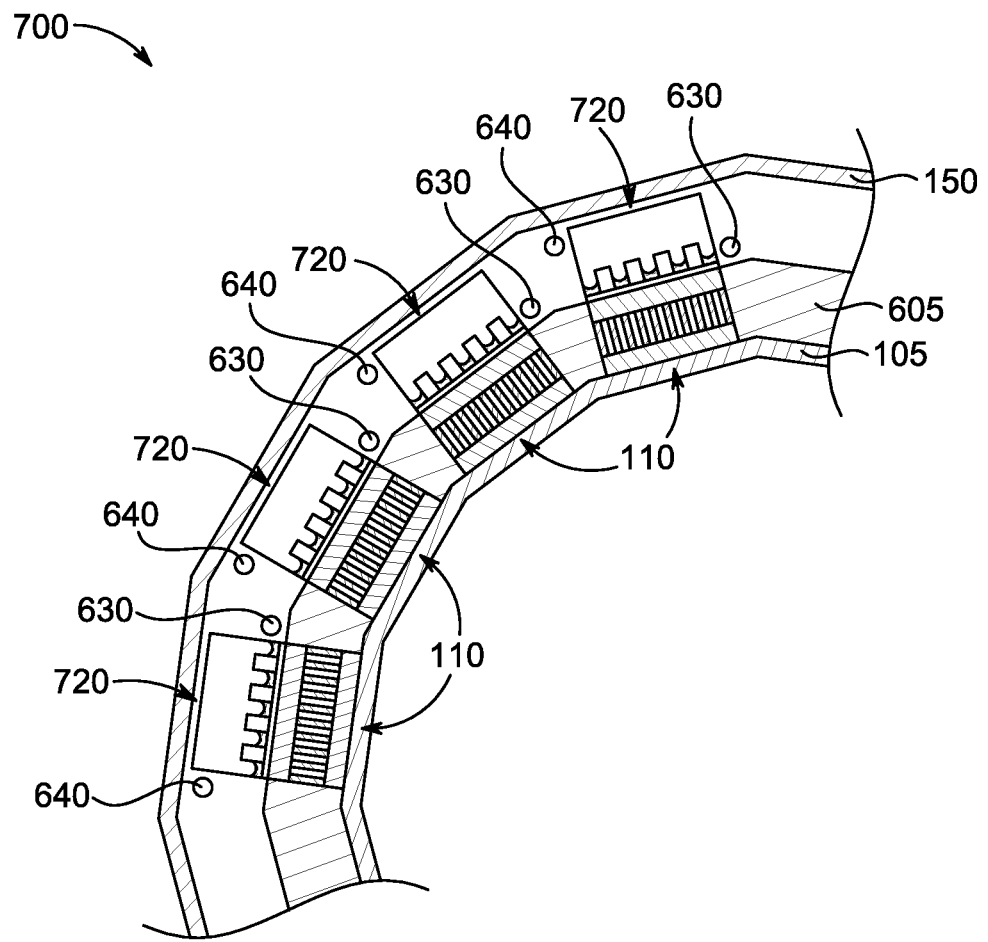
FIGS. 7-9 are partially schematic cross-sectional views of wearable heat transfer devices, in accordance with embodiments of the present technology.

FIG. 7 is a cross-sectional view of a wearable heat transfer device 700 ("the device 700"), in accordance with embodiments of the present technology. The device 700 includes features generally similar to those described with reference to FIGS. 6A and 6B, and can include the flexible support unit 105, the flexible matrix 605, the TECs 110 embedded within the flexible matrix 605, a fluid distribution network 720, the working fluid inlet passage 630 configured to provide the liquid working fluid to the fluid distribution network 720, the working fluid outlet passage 640 configured to collect the working fluid (e.g., the vapor working fluid ($WF_V$)) from the fluid distribution network 720, and the insulation member 150 radially outward of the fluid distribution network 720. The fluid distribution network 720 can be generally similar to and include the functionality of the fluid distribution network 620 (FIGS. 6A and 6B), fluid distribution network 520 (FIGS. 5A and 5B), and/or evaporators 120 (FIGS. 1-4) previously described. Relative to the fluid distribution network 620, the fluid distribution network 720 does not have multiple array portions spaced apart from one another. As such, the fluid distribution network 720 can have a relatively smaller footprint than that of the fluid distribution network 620 and thus allow the device 700 to be relatively more flexible and/or bendable. In practice, this can enable a better fit of the device 700 on the user and/or ensure better thermal contact between the TECs 110 and the target area of the user.

Figure 8:
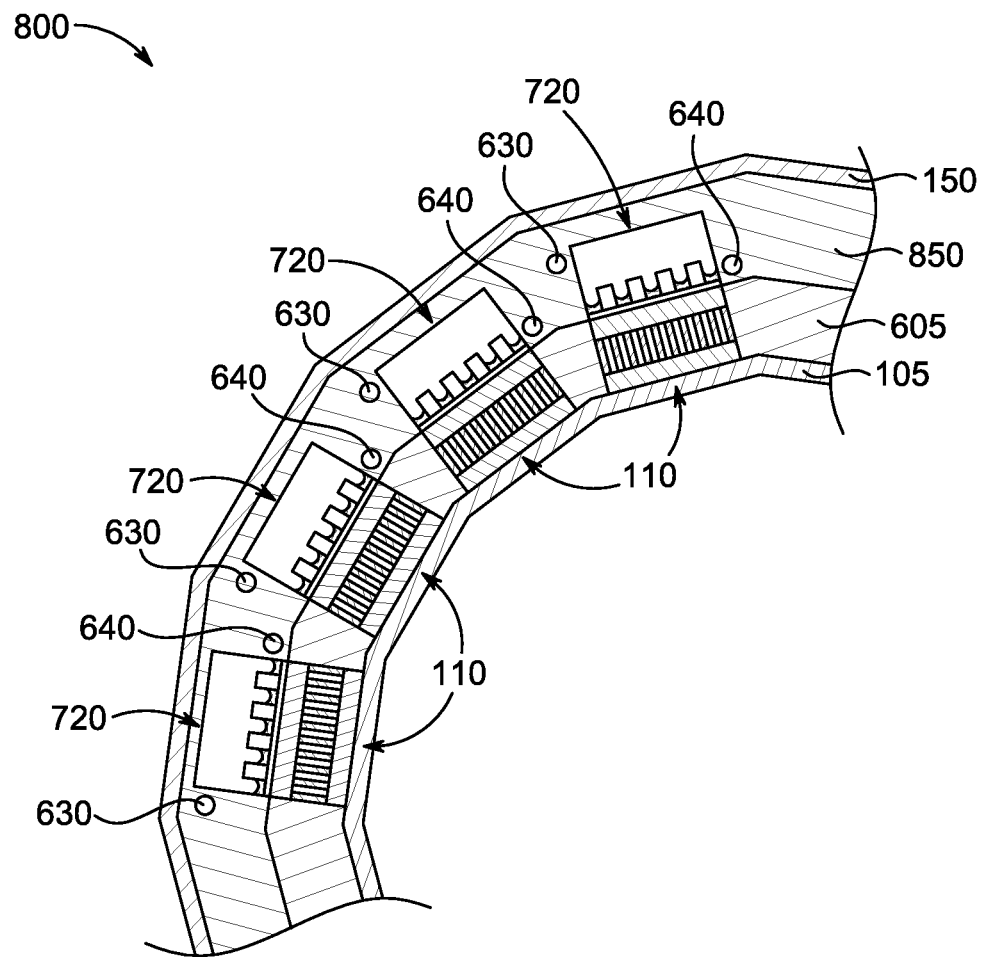

FIG. 8 is a cross-sectional view of a wearable heat transfer device 800 ("the device 800"), in accordance with embodiments of the present technology. The device 800 includes features generally similar to those described with reference to FIG. 7, and can include the flexible support unit 105, the flexible matrix 605, the TECs 110 embedded within the flexible matrix 605, the fluid distribution network 720, the working fluid inlet passage 630 configured to provide the liquid working fluid ($WF_L$) to the fluid distribution network 720, the working fluid outlet passage 640 configured to collect the working fluid (e.g., a vapor working fluid ($WF_V$)) from the fluid distribution network 720, and the insulation member 150 radially outward of the fluid distribution network 720. The device 800 can further include a flexible support material 850 positioned between the insulation member 150 and the flexible matrix 505 and surrounding the heat transfer system. Stated differently, the fluid distribution networks 720, the liquid distribution passage 530, and/or the vapor collection passage 540 can be embedded within the flexible support material 850. The flexible support material 850 can comprise an elastic material and/or have a flexibility similar to that of the flexible support unit 105 or flexible matrix 505. In some embodiments, the flexible support material 850 can comprise a non-conductive, insulative material such as a foam, gel, and/or composite. In practice, the flexible support material 850 is configured to provide additional structural support to the device 500 when worn by a user.

Figure 9:
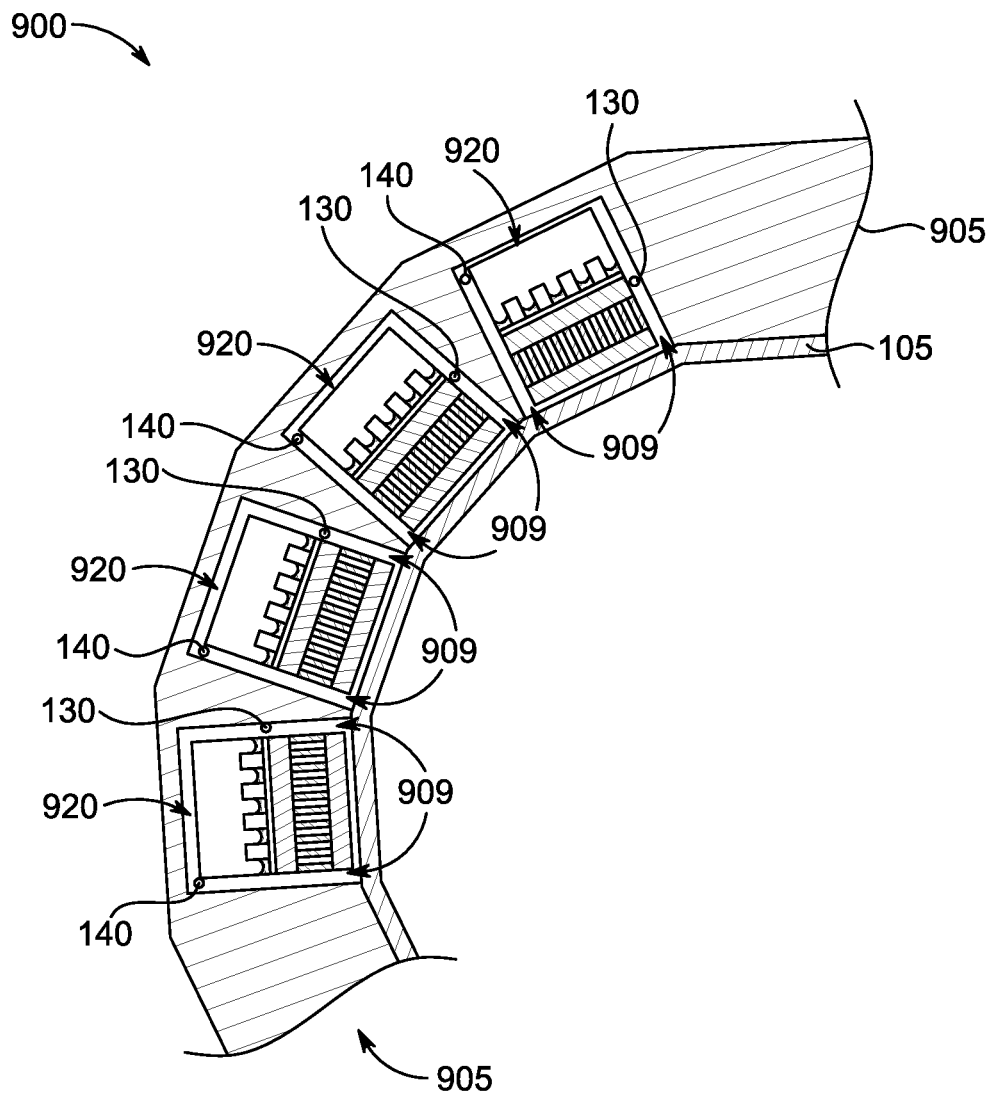

FIG. 9 is a cross-sectional view of a wearable heat transfer device 900, in accordance with embodiments of the present technology. The device 900 includes features generally similar to those described with reference to FIG. 7, and can include the flexible support unit 105, the TECs 110 embedded over and thermally coupled to the flexible support unit 105, the fluid distribution networks 720 over and thermally coupled to corresponding ones of the TECs 110, the liquid distribution passage 530 configured to provide the liquid working fluid ($WF_L$) to the fluid distribution networks 720, and the vapor collection passage 540 configured to collect the vapor working fluid ($WF_V$) from the fluid distribution networks 720. As shown in FIG. 9, the device 900 can further include a flexible backing or matrix 905 disposed over the flexible support unit 105 and surrounding the TECs 110. The flexible matrix 905 can include pockets 909 (e.g., openings or voids) configured to encase individual ones of the fluid distribution networks 120 and the TECs 110. The flexible matrix 905 can comprise an elastic material and/or have a flexibility similar to that of the flexible support unit 105. In some embodiments, the flexible matrix 905 can comprise a non-conductive, insulative material such as a foam, gel, and/or composite material. In practice, the flexible matrix 905 is configured to provide additional structural support to the device 500 when worn by a user. Advantageously, the device 900 may not include an insulation layer or member radially outward of the flexible matrix 905, as the flexible matrix 905 can act as an insulative barrier itself.

III. Wearable Heat Transfer Device Areas of Treatment

Figure 10A:
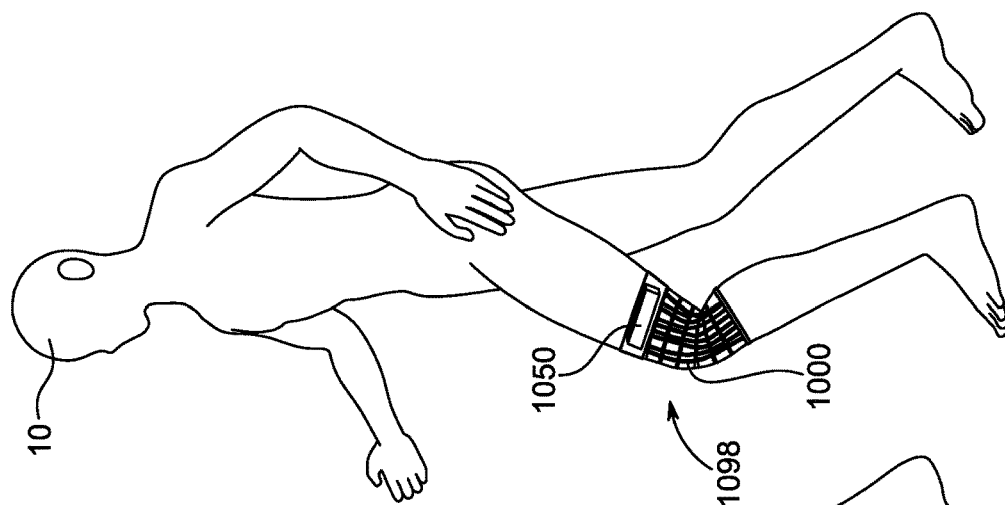
FIG. 10A is a partially schematic view of a heat transfer device being worn by a mammal, in accordance with embodiments of the present technology.
Figure 11:
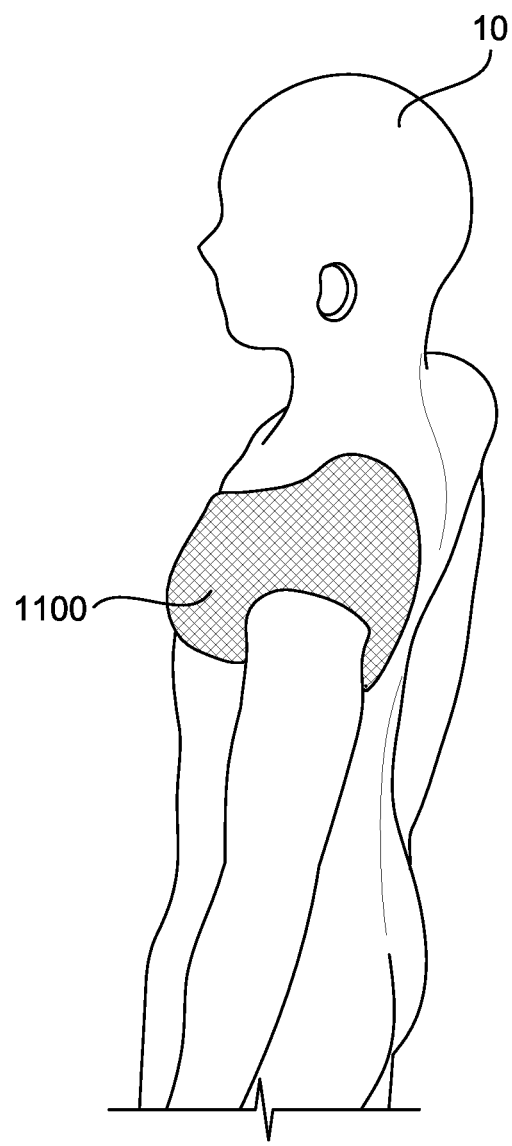
FIGS. 11-19 are partially schematic views of heat transfer devices being worn by a mammal at various target areas, in accordance with embodiments of the present technology.
Figure 12:
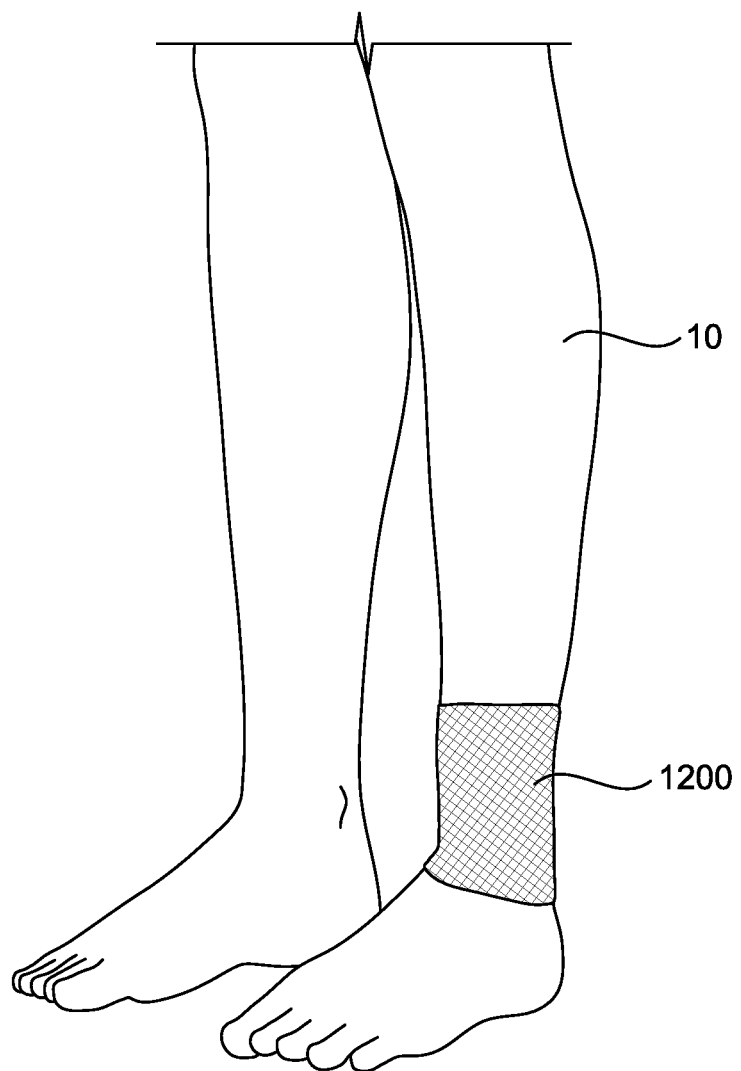
Figure 13:
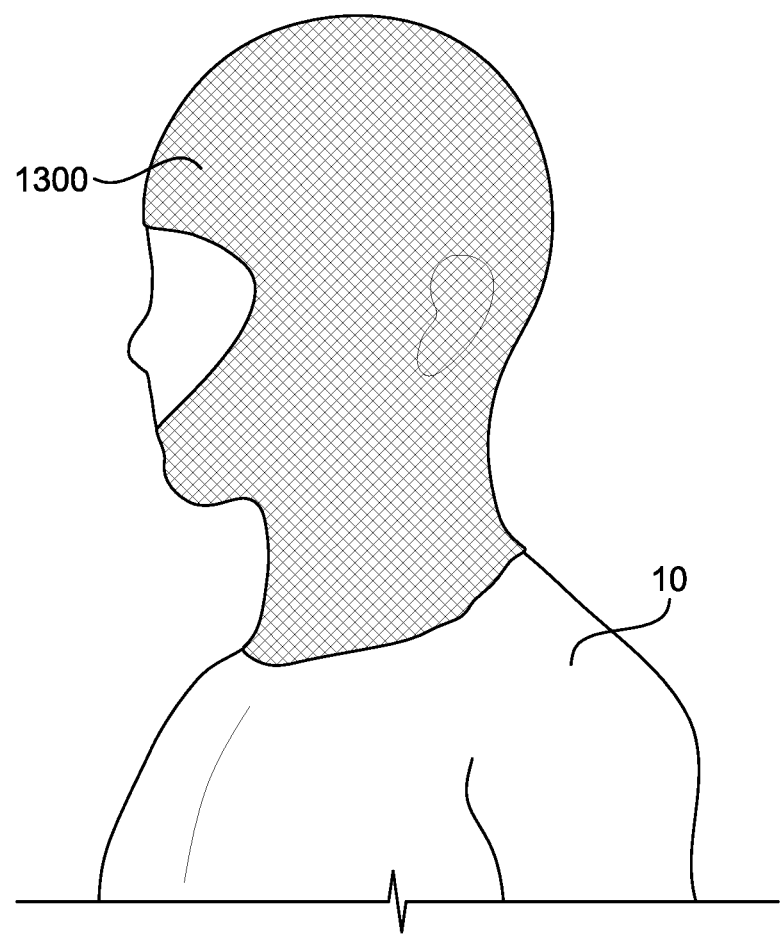
Figure 14:
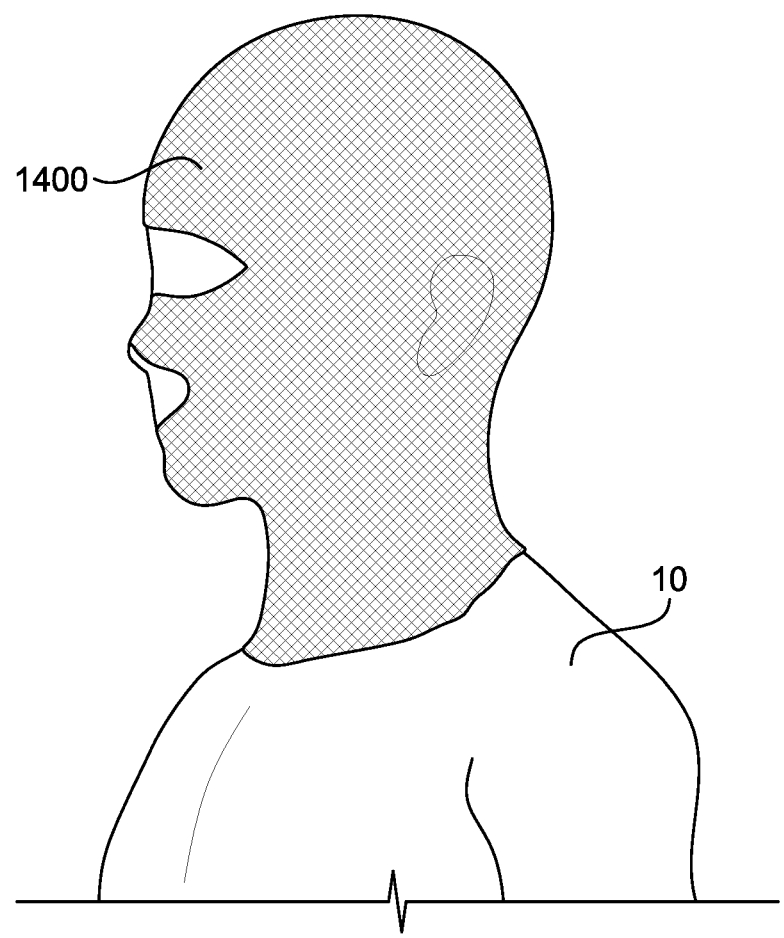
Figure 15:
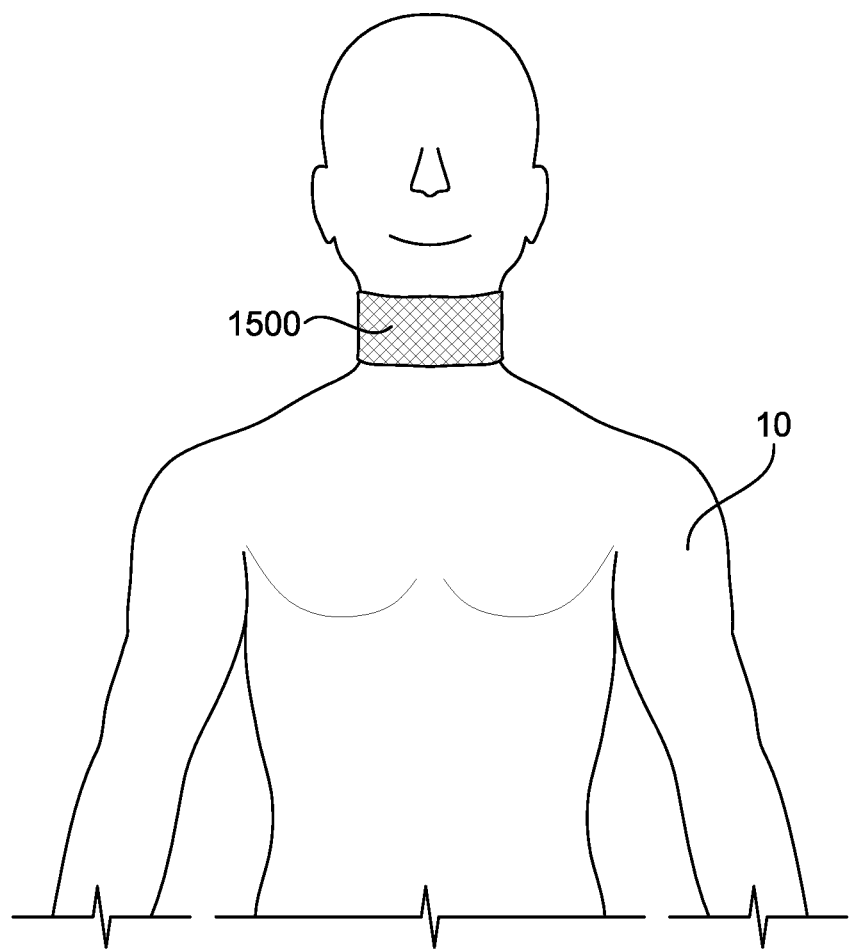
Figure 16:
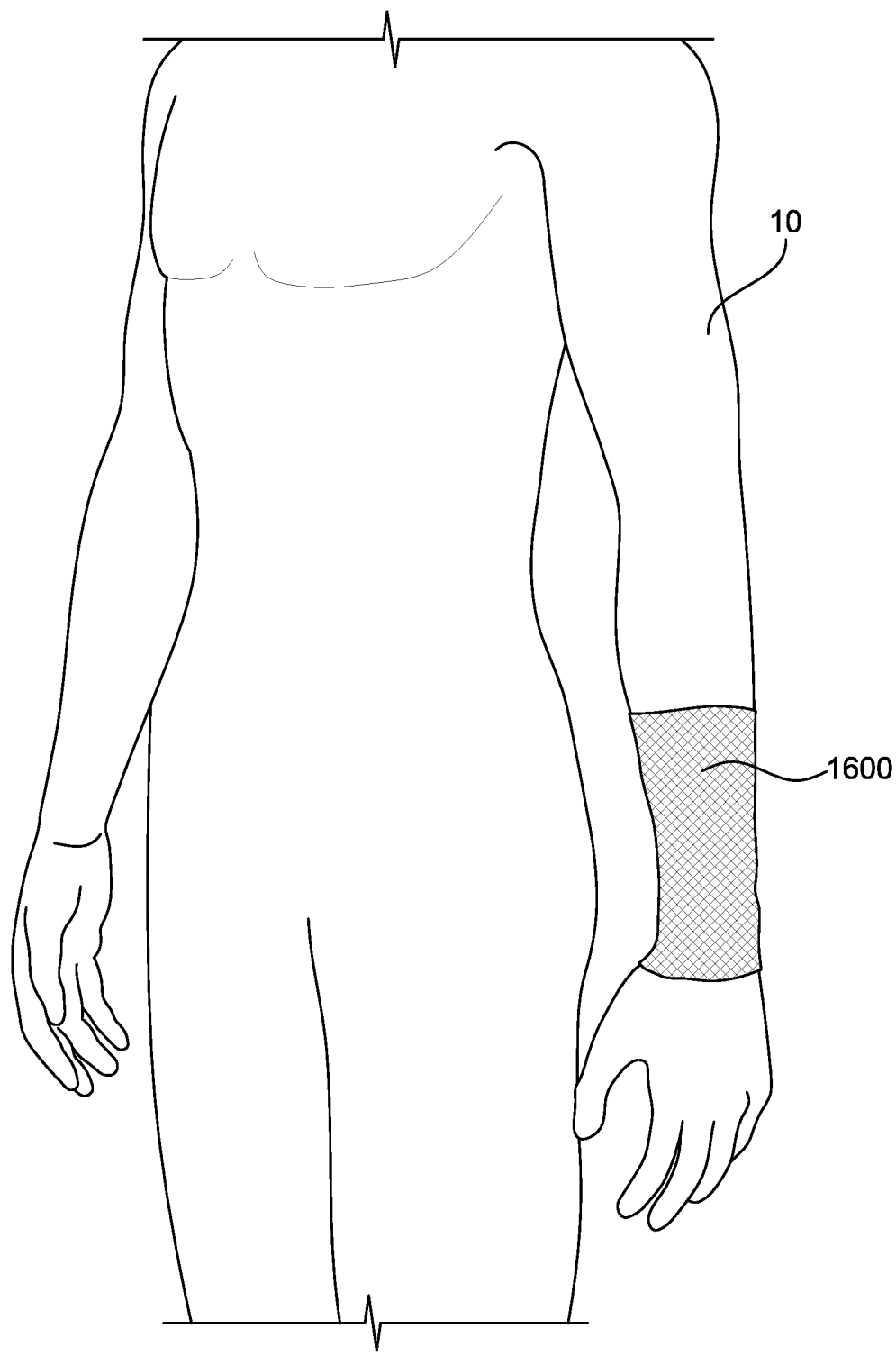
Figure 17:
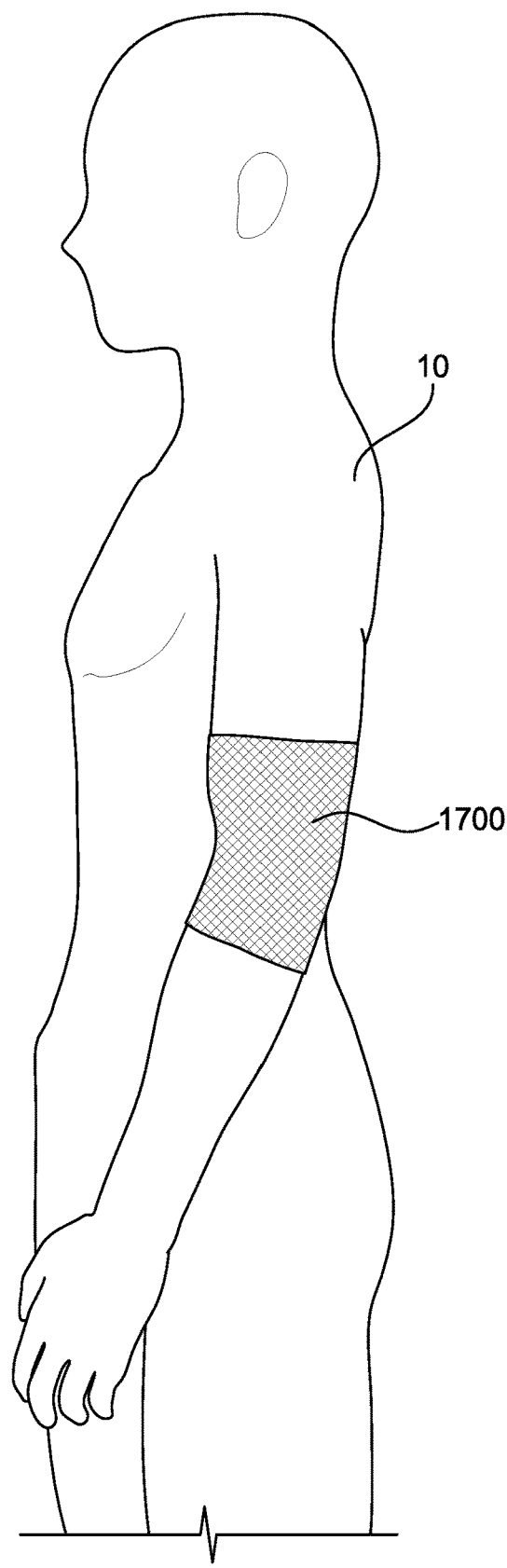

The wearable heat transfer devices disclosed herein can be designed for different target areas and/or body parts, including the head, neck, chest, shoulder, upper back, lower back, upper arm, lower arm, wrist, waist, upper leg, lower leg, feet, hands, etc. The devices can be placed on the target area utilizing fasteners, adhesives, straps, tape (e.g., Velcro), belts, or any other means known and practiced in the relevant art. Some of the target areas are illustrated in FIGS. 10A-19, which are various partially schematic views of the heat transfer devices being worn by a mammal 10. The devices shown in FIGS. 10A-19 can correspond to any of the devices (e.g., devices 50, 100, 600, 700, 800, 900) described herein, and thus can each include some or all of the elements (e.g., the flexible support unit, TECs, fluid distribution network, evaporators, etc.) described elsewhere herein. With reference to these figures, the device 1000 shown in FIG. 10A is disposed around a knee region of the mammal 10, the device 1100 shown in FIG. 11 is disposed over a shoulder region of the mammal 10, the device 1200 shown in FIG. 12 is disposed around an ankle and/or lower leg region of the mammal 10, the device 1300 is disposed around head and neck regions of the mammal 10, the device 1400 is disposed around head, neck, and facial (e.g., nasal) regions of the mammal 10, the device 1500 is disposed around a neck region of the mammal 10, the device 1600 is disposed around a wrist and/or lower arm region of the mammal 10, the device 1700 is disposed around an elbow region of the mammal 10, the device 1800 is disposed around lower and upper body regions of the mammal 10, and the device 1900 is disposed around lower body, upper body, and head regions of the mammal 10.

Figure 10B:
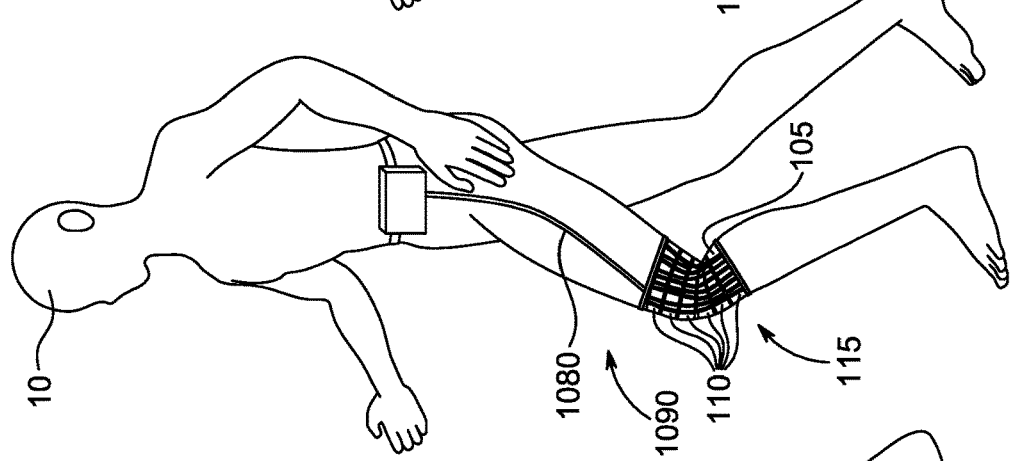
FIGS. 10B-10D are partially schematic views of a heat transfer system including the heat transfer device of FIG. 10A, in accordance with embodiments of the present technology.
Figure 10C:
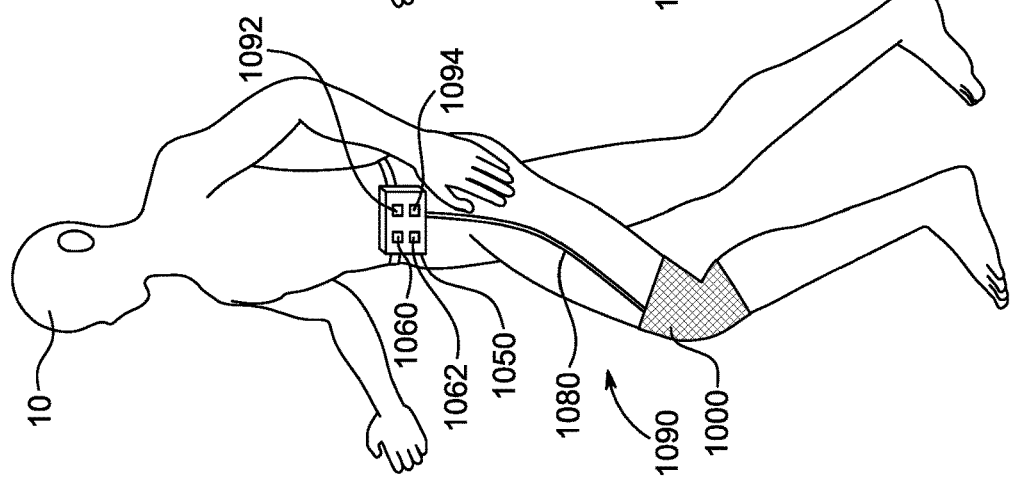
Figure 10D:
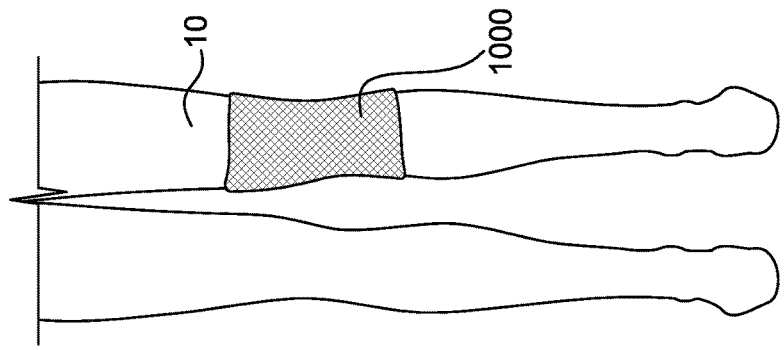

FIGS. 10B-10D are partially schematic views of a heat transfer system 1090 including the heat transfer device 1000 and a plurality of subsystems or other device elements. In addition to the device 1000, the systems described with reference to FIGS. 10B-10D can apply to or be incorporated with any of the devices (e.g., the device 50, 100, 400, 500, 600, 700, 800, 900, 1100, 1200, 1300, 1400, 1500, 1600, 1700, 1800, 1900) disclosed herein. The subsystems and/or device elements can be integrated into a package 1050 secured to the mammal 10 (e.g., at a waist region). The device 1000 can include a heat exchanger 1060 and one or more pumps 1062, which can both be stored in the package 1050. The heat exchanger 1060 can include a condenser (e.g., the condenser 160), e.g., if the heat transfer system of the device 1000 is a two-phase system, or a liquid-air heat exchanger (e.g., the heat exchanger 560), e.g., if the heat transfer system of the device 1000 comprises is a single-phase system. Storing the heat exchanger 1060 physically above the device 1000 can advantageously provide additional head pressure to the working fluid supplied to the device 1000 and help ensure adequate flow of the working fluid to the fluid distribution network of the device 1000. The one or more pumps 1062 can be fluidically coupled to the heat exchanger 1060 and the heat transfer system of the device 1000, and can ensure adequate flow of the working fluid throughout the heat transfer system.

The heat transfer system 1090 can further include a power source 1092 operably coupled to the device 1000 and configured to provide power to the TECs 110 (FIG. 10C). The power source 1092 can enable the TECs 110 to be set to a particular temperature for heating and/or cooling purposes. In some embodiments, the power source 1092 can include a portable energy storage device (e.g., a battery).

The heat transfer system 1090 can further include a controller and/or electronic component(s) 1094 operably coupled to the device 1000, power source 1092, and other subsystems. In some embodiments, the controller and/or electronic component(s) 1094 can include a transmitter and/or receiver enabling the controller 1094 to communicate (e.g., wirelessly communicate) with a remote user interface (e.g., on a mobile device and/or remote network) and/or the device 1000. In some embodiments, the controller 1094 can be configured to operate the device 1000 in one of a plurality of operating modes (e.g., a cooling mode, a heating mode, or both), and/or provide a process value (e.g., a set temperature) at which the device 1000 is configured to operate. In some embodiments, the controller 2294 can provide a setpoint temperature within a range of 40° C. to −20° C. (e.g., 35° C., 20° C., 0° C., −10° C., etc.) to the device 1000 such that the TECs (e.g., the first or second side of the TECs) are configured to operate at the setpoint temperature. Additionally or alternatively, the controller 1094 can be configured to receive inputs from sensors (e.g., sensors 180a-f; FIG. 2) on the device 1000 and control the device based on the received inputs. For example, the controller 1094 can determine any abnormalities of the operating device and automatically generate indications of the abnormalities and/or adjust the operating parameters of the device. Additionally or alternatively, the controller 1094 may utilize artificial intelligence and/or machine learning to adjust power and/or other control parameters, e.g., based on previous treatments used for the same user or a group of users.

In some embodiments, the heat transfer system 1090 can include a conduit 1080 extending from the package 1050 to the device 1000. The conduit 1080 can include (i) fluid transport lines, e.g., extending from and fluidically coupling the heat exchanger 1060 and/or one or more pumps 1062 to the fluid distribution network of the device 1000, (ii) power lines, e.g., extending from and operably coupling the power source 1092 to the TECs, and/or (iii) other wires, e.g., extending from and operably coupling the controller to sensors on the device 1000. In some embodiments, the conduit 1080 is omitted, e.g., as shown and described with reference to FIG. 10D. Additionally or alternatively, in some embodiments in which the conduit 1080.

FIG. 10C illustrates another view of the system 1090 shown and described with reference to FIG. 10B, but omits an outer cover of the device 1000 for illustrative purposes. As such, the TECs 110, flexible support unit 105, and heat transfer system 115 previously described with reference to others figures are shown schematically.

FIG. 10D illustrates another system 1099 which is generally similar to the system 1090 shown and described with reference to FIGS. 10B and 10C, but the package 1050 and its components (e.g., the heat exchanger 1060, pump 1062, power source 1092, and/or controller 1094) are embedded within the device 1000, e.g., physically above the TECs or majority of device components.

The systems 1090, 1099 described with reference to respective FIGS. 10C and 10D are shown to be operably coupled to a single device. In some embodiments, the system 1090 or system 1099 can be operably coupled to multiple devices, e.g., disposed on or around different target areas of the mammal 10. For example, in some embodiments the system 1090 (or system 1099) can be operatively coupled to a first device disposed around the knee region and a second device disposed over the shoulder region. In such embodiments, the system 1090 (or system 1099) can individually control the first device independent (and individual TECs 110 thereon) from the second device, or vice versa.

Each of the devices shown in FIGS. 10A-19 can be used to treat a number of underlying conditions experienced at the target area, such as pain, swelling, overheating (e.g., for cancer patients), diminished blood perfusion, diminished nerve connectivity, and/or stroke, amongst other conditions. Moreover, each of the devices shown in FIGS. 10A-19 can be designed based on the particular area of treatment. That is, in addition to designing the device to conform to the geometry of the target area, as shown in FIGS. 10A-19, other characteristics (e.g., thickness, flexibility, density of TECs, compressive force applied to the target area, etc.) may be incorporated into the design based on the target area. For example, the device 1000 disposed around the knee region of the mammal 10 can be designed to have increased flexibility at the knee joint area of the device 1000 expected to experience the most bending, and thus may include less TECs adjacent that area. In some embodiments, the design may be based on the expected treatment to be provided via the particular device. For example, the devices 1300 and 1400 disposed around the head regions of the mammal 10 can be particularly useful for treating patients that have experienced a stroke and that need relatively quick cooling of the head region following the stroke event (e.g., in the ambulance or at the hospital). Accordingly, the devices 1300 and 1400 may be preprogrammed with an operating mode configured to thermally treat a patient that has recently experienced a stroke or other relevant condition.

IV. Ocular Region Heat Transfer Devices and Associated Systems and Methods

Cooling the tissue of mammals at the ocular region, or more particularly the under-eye-tissue, can be an effective treatment for common eye issues, including under eye puffiness, under eye bags, dark circles, and eye hollows, amongst other known eye issues. For example, eye puffiness, which is the result of periorbital edema and causes fluid buildup under the eye, can be treated by cooling the area to reduce inflammation. Under eye bags are the result of fat build up under the eyes, and can be treated by a procedure known as cryolipolysis, which applies temperatures less than 5° C. to freeze and kill corresponding fat cells. Dark circles can be eliminated by shrinking the dilated blood vessels under the eyes skin by cooling, which influences vasoconstriction and squeezes down the vessel to reduce the appearance of the dark circles. Round hollows around the eyes arise due to muscle tensions due to long hours working with computers and phones, and cooling around the eyes can relax these muscles and help reduce the pressure on the eyes muscle and consequently eliminates the hollows.

While the benefits of cooling are generally known, the available cooling products for performing such cooling are limited and not very effective. Cold compresses, for example, are the primary cooling products for the ocular region, but do not provide critical features, including (i) sufficient cooling capacity, (ii) the ability to provide cooling treatment at difference temperatures, and (iii) a responsive temperature control system. Additionally, cold compresses are bulky and are thus difficult to place on small areas such as under the eye with good thermal contact.

Embodiments of the present technology address these and other issues associated with cooling the ocular region with a heat transfer device and/or system that is compact, lightweight, and configured to be disposed at an ocular region of a user/mammal. As described in additional detail elsewhere herein (e.g., with reference to FIGS. 20A-21B), the heat transfer device can include improved cooling capacity, improved thermal contact between the device and user/mammal, and the ability to precisely control temperature of the adjacent under-eye area.

Figure 20B:
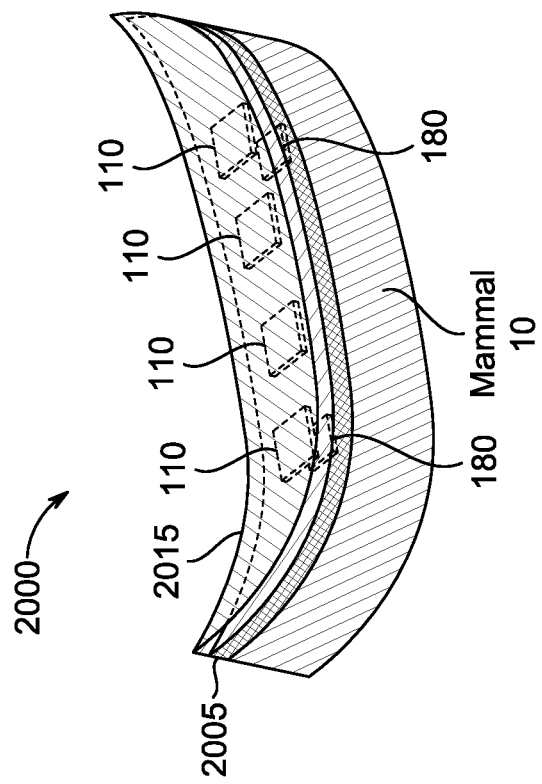
FIG. 20B is an isometric view of the heat transfer device of FIG. 20A in an assembled form.
Figure 20A:
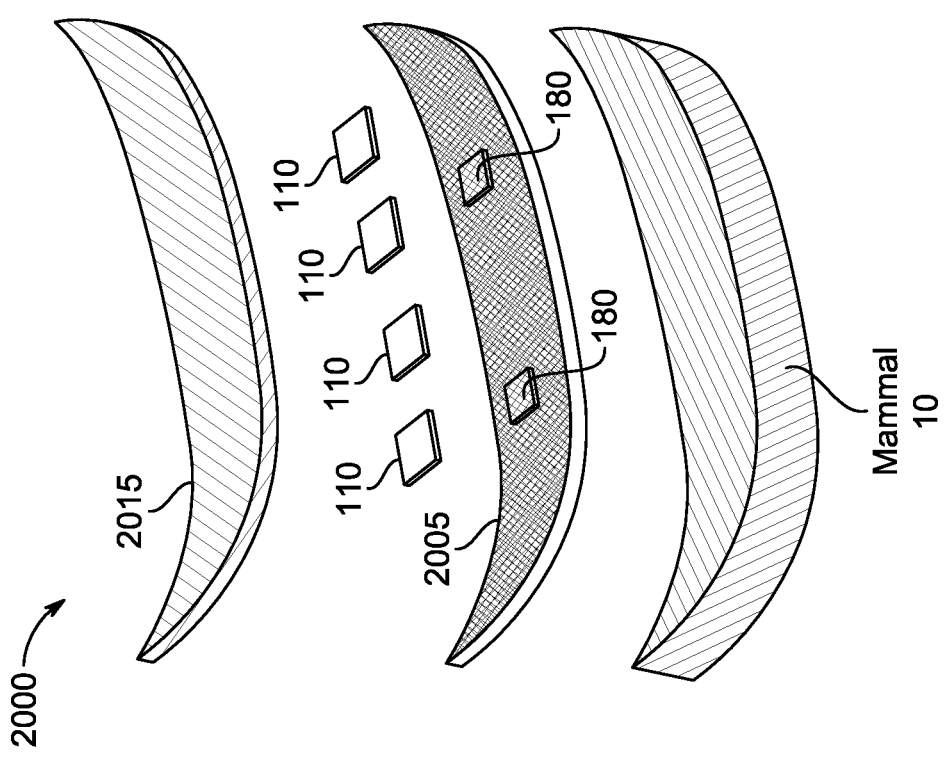
FIG. 20A is a schematic isometric exploded view of a heat transfer device, in accordance with embodiments of the present technology.

FIG. 20A is a schematic isometric exploded view of a heat transfer device 2000 ("the device 2000"), and FIG. 20B is an isometric view of the device 2000 of FIG. 20A in an assembled form. Referring to FIGS. 20A and 20B together, the device 2000 can include (i) a thermally conductive member or plate 2005 configured to be disposed against and thermally coupled to a target area of the ocular region of a mammal 10, (ii) a plurality of TECs 110 thermally coupled to and disposed over the thermally conductive member 2005, (iii) one or more sensors 180 configured to sense a temperature of the thermally conductive member 2005, target area, and/or individual ones of the TECs 110, and (iv) a heat transfer system 2015 thermally coupled to the TECs 110 and disposed over the thermally conductive member 2005. As shown in FIGS. 20A and 20B, the thermally conductive member 2005 and/or the heat transfer system 2015 can have a crescent shape enabling the device 2000 to be disposed under and relatively close to the eye, and to complement the shape of the eye. In some embodiments, upper and lower surfaces of the thermally conductive member 2005 and/or the heat transfer system 2015 can have a concave shape. As shown in FIGS. 20A and 20B, the thermally conductive member 2005 and/or the heat transfer system 2015 can have the same shape, e.g., to limit an overall footprint of the device 2000.

The thermally conductive member 2005 is thermally coupled to and extends between each of the TECs 110. The thermally conductive member 2005 can act as a heat spreader to enhance heat transfer to and/or from the target area in the regions between the TECs 110. The thermally conductive member 2005 can comprise conductive materials and/or biocompatible materials, including metals, metallic alloys, coatings, polymers, silicone, and/or combinations thereof. In some embodiments, the thermally conductive member 2005 can correspond to the flexible support unit 105 and thus can include any of the features and functionality previously described with reference to FIGS. 1A and 1B.

The heat transfer system or unit 2015 is shown schematically in FIGS. 20A and 20B, and can include features generally similar or identical to the heat transfer system 115 described with reference to FIGS. 1A-4 above or the heat transfer system 515 described with reference to FIGS. 5A and 5B above. Accordingly, the heat transfer system 2015 can be a single or two-phase heat transfer system. For those embodiments comprising a two-phase system, the heat transfer system 2015 can include an array of fluid distribution networks (e.g., the evaporators 120; FIG. 1B) each thermally coupled to a corresponding one of the TECs 110, a liquid distribution passage (e.g., the liquid distribution passage 130; FIG. 1B) configured to provide a working fluid in a liquid phase ($WF_L$) to each of the evaporators, a vapor collection passage (e.g., the vapor collection passage 140; FIG. 1B) configured to receive the working fluid in a vapor phase ($WF_V$) from each of the evaporators, and a condenser (e.g., the condenser 160; FIG. 1B). The heat transfer system can comprise a closed loop two-phase system, wherein flow of the working fluid through the system is driven by heat transferred from the TECs 110 to the individual evaporators, and/or by pumps, gravity, or other means. In some embodiments, flow of the working fluid through the heat transfer system can be driven by capillary forces induced by microfeatures (e.g., pillars, pins, or walls) that form channels present within chambers of the evaporators that drive the liquid phase of the working fluid from inlets of the chambers toward the outlets of the chambers.

The TECs 110 can include any of the features and functionality of the TECs 110 described with reference to FIGS. 1B-4. As such, the TECs 110 of the device 2000 can provide precise, controllable, and/or localized temperature control at the interface between the target ocular area and the device 2000. As previously described, the TECs 110 are thermally coupled to the mammal 10, and can be set to a particular temperature and/or predetermined temperature profile (e.g., constant temperature profile, temperature cycle profile, and/or time based profile) by a controller (e.g., the controller 2294; FIG. 22) to cool and/or heat the adjacent target ocular area of the mammal 10. In some embodiments, individual TECs 110 are controlled by the controller independent of other individual TECs 110, e.g., to provide localized and variable control when desired. For example, the first side of the TECs 110 facing the mammal 10 or the second side of the TECs 110 facing the heat transfer system 2015 can be set to a temperature within a range of 10° C. to −5° C. (e.g., 5° C., 0° C., etc.). In some embodiments, the TECs 110 can be configured to reach a desired temperature within a predetermined time (e.g., no more than 10 seconds, 20 seconds, 30 seconds, 60 seconds, 120 seconds, 240 seconds or 600 seconds).

Figure 18:
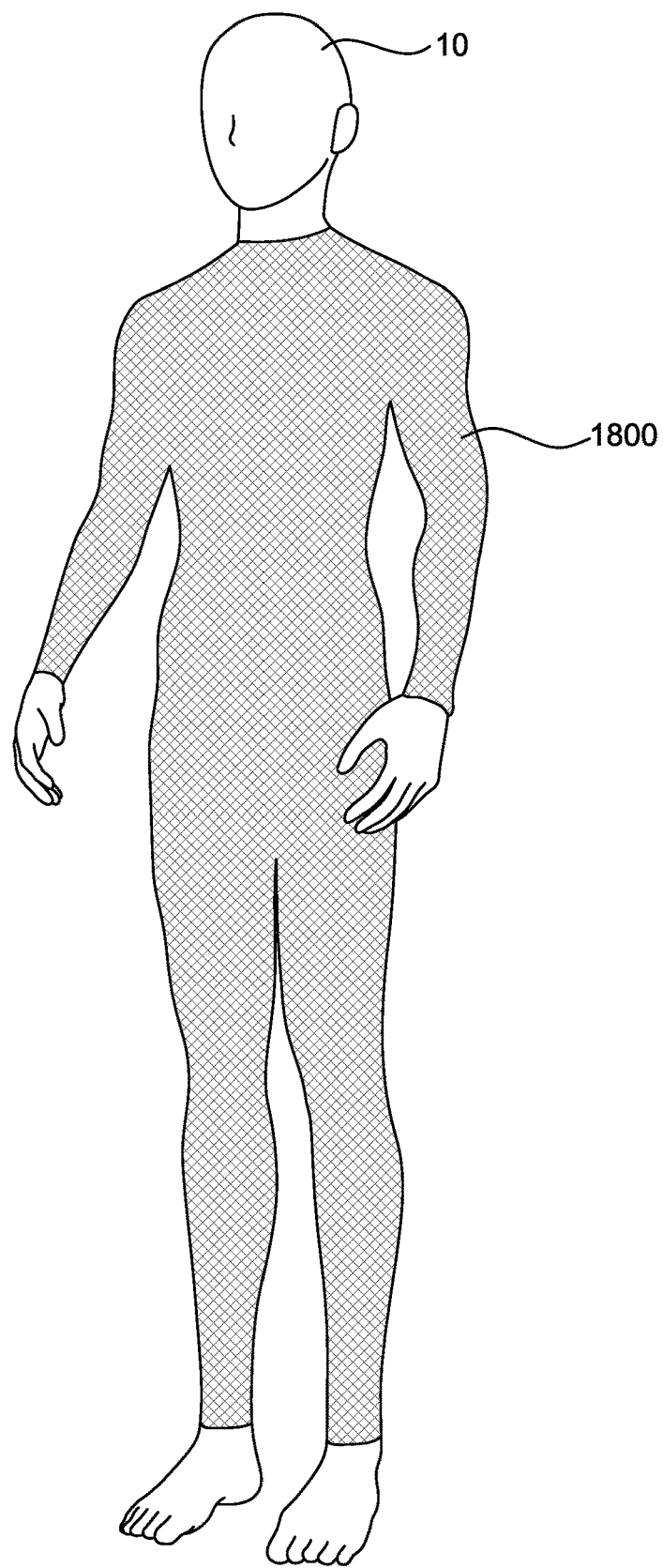
Figure 19:
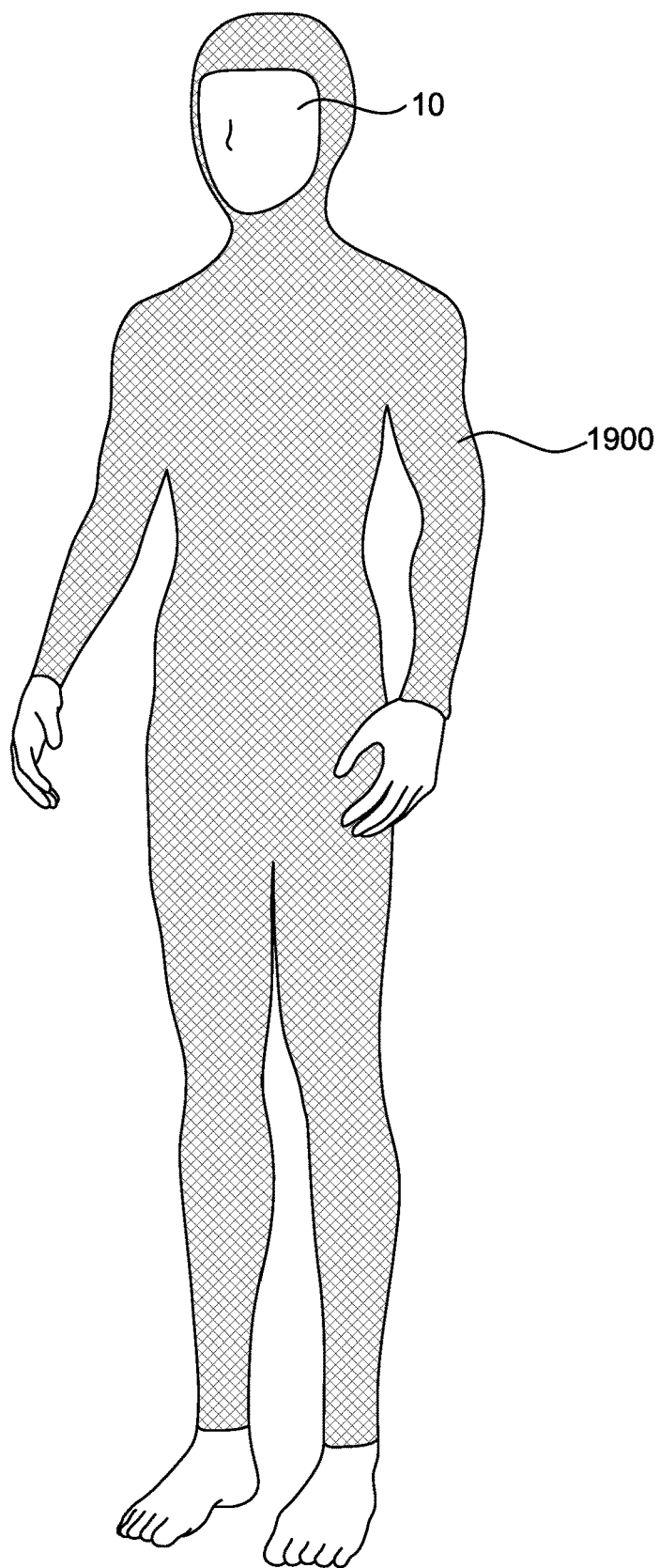

The TECs 110 can be placed in a heating mode, a cooling mode, or cycle between cooling and heating to control the temperature at the target ocular area. Heat flow across an individual TEC 110 can be a function of temperature difference between its two side and the electric power input provide to the individual TEC 110 from a power source (e.g., power 1892; FIG. 18) The mode and/or operation of the mode can be selected based on predetermined cycle times and/or temperature feedback, e.g., from the sensors 180.

When in the heating mode, the TECs 110 can provide heat to the target area of the mammal 10 (e.g., via the thermally conductive member 2005) by heating the first side of the TECs 110 which causes the second sides of the TECs 110 to cool. In some embodiments, the device 2000 can further comprise additional resistive heaters (not shown in FIG. 20A) that can be controlled via the controller and configured to heat the adjacent target ocular area of the mammal 10. When in the cooling mode, the evaporators of the heat transfer system 2015 are configured to remove heat from hotter second sides of the TECs 110 and thereby enable the first sides of the TECs 110 to cool the adjacent target ocular area of the mammal 10. As such, in the cooling mode heat flows from the target ocular area of the mammal 10 in a radially outward direction to the TECs 110 and then to the evaporators of the heat transfer system 2015. As previously described, the TECs 110 can also cycle between the cooling and heating modes, which can enhance blood flow and perfusion to the target ocular area. Additional details regarding individual TECs 110 are provided elsewhere herein (e.g., with reference to FIGS. 1B, 3 and 4).

The sensors 180 can includes any of the features and functionality of the sensors 180 described with reference to FIG. 2. As such, the sensors 180 of the device 2000 can be configured to measure a desired parameter (e.g., temperature, pressure, etc.) of the thermally conductive member 2005, individuals TECs 110, and/or the target ocular area. Each of the sensors 180 can be in communication with the controller and be used to verify and/or improve safety (e.g., prevent overcooling and/or high pressure zones), efficacy, and operation of the device 2000 via the controller.

The device 2000 can be placed at the target ocular area of the mammal 10 using any fastener, adhesive, strap, tape (e.g., Velcro), belt, or other know means. However, since the under eye skin is relatively sensitive and thin, using any fastener that applies pressure (e.g., vacuum, straps, Velcro, etc.) may cause damage to the skin or tissue. Also, the device 2000 can be displaced with minor motion of the head, and it may not be practical for users/mammals to refrain from moving during treatment. Accordingly, as shown FIGS. 21A and 21B, the device 2000 may be disposed against the target ocular area using an ocular device that the device 2000 is coupled to. The ocular device can be configured to improve the thermal contact between the and device 2000 at the target ocular area.

Figure 21A:
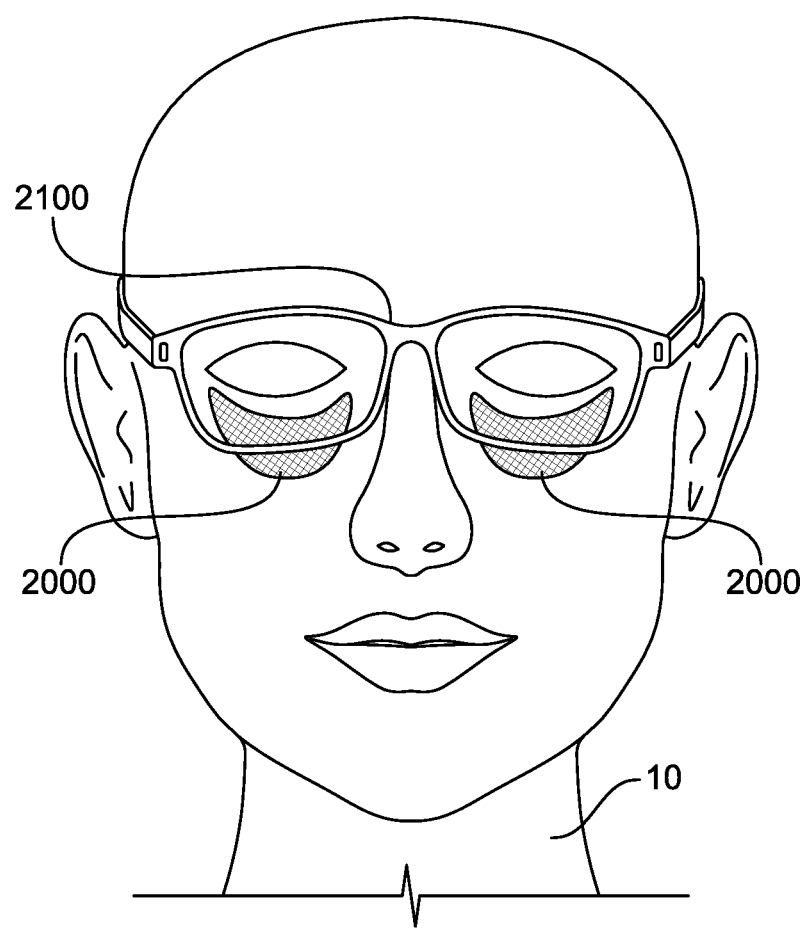
FIG. 21A is a partially schematic front view of an ocular device coupled to the heat transfer device of FIGS. 20A and 20B, in accordance with embodiments of the present technology.
Figure 21B:
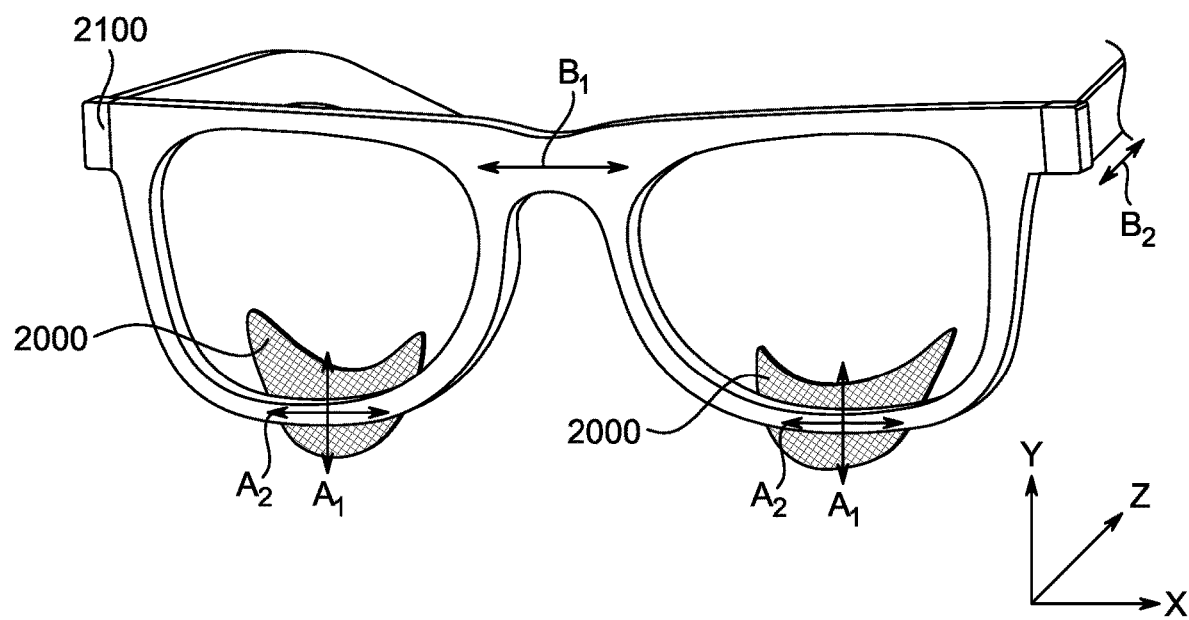
FIG. 21B is an isometric view of the ocular device of FIG. 21A.

FIG. 21A is a partially schematic front view of an ocular device 2100 coupled to the device 2000 of FIGS. 20A and 20B, and FIG. 21B is an isometric view of the ocular device 2100 of FIG. 21A. As shown in FIG. 21A, the ocular device 2100 is worn by the mammal 10 and can include a frame coupled to the devices 2000. When the ocular device is worn by the mammal 10, the device or devices 2000 are disposed between the frame of the ocular device 2100 and the mammal 10 to place the devices 2000 in thermal contact with the mammal 10. In doing so, the devices 2000 can be held in place to enable therapy via the devices 2000 while the mammal has the freedom the move his or her head without risk of the devices 2000 being displaced. In some embodiments, the frame can include all or part of the heat transfer system 615 (FIGS. 20A and 20B) of the device 2000. For example, the liquid distribution passage, the vapor collection passage, and/or the condenser portions of the heat transfer system 2015 previously described can be incorporated into the frame of the ocular device 2100

As shown in FIG. 21B, the ocular device 2100 can be adjusted to accommodate different mammals 10 and allow for better thermal contact with the device 2000. For example, the frame of the ocular device 2100 can be adjusted along the x-axis as illustrated by $B_1$ and/or along the y-axis as illustrated by $B_2$. Additionally or alternatively, coupling of the device 2000 to the ocular device 2100 (e.g., the position of the device 2000 relative to the ocular device 2100) may be adjusted along the y-axis as illustrated by $A_1$ and/or along the x-axis as illustrated by $A_2$. In doing so, the device 2000 can be placed to enable optimal thermal contact with the target ocular area.

Any one of the heat transfer devices 100, 500, 600, 700, 800, 900, 1000, 1100, 1200, 1300, 1400, 1500, 1600, 1700, 1800, 1900, 2000 described elsewhere herein with reference to FIGS. 1-21B can be incorporated into a myriad of other and/or more complex systems, a representative example of which is system 2290 shown schematically in FIG. 22. The system 2290 can include a heat transfer device (e.g., the heat transfer device 100, 500, 600, 700, 800, 900, 1000, 1100, 1200, 1300, 1400, 1500, 1600, 1700, 1800, 1900, 2000), a power source 2292 (e.g., a portable power source, battery, etc.) operatively coupled to the device (e.g., to the TECs of the device), a controller 2294 (e.g., a processor) operatively coupled to the device and the power source 2292, a user interface 2296 operatively coupled to the controller 2294 and the power source 2292, as well as other subsystems. The system 2290 can perform any of a wide variety of functions, such as memory storage, data processing, and/or other suitable functions.

The controller 2294 can be configured to operate the device in one of a plurality of operating modes (e.g., a cooling mode, a heating mode, or both), and/or provide a process value (e.g., a set temperature) at which the device is configured to operate. As previously described with reference to FIG. 1 for example, the controller 2294 can provide a setpoint temperature within a range of 40° C. to −20° C. (e.g., 35° C., 20° C., 0° C., −10° C., etc.) to the device such that the TECs 110 (e.g., the first or second side of the TECs) are configured to operate at the setpoint temperature. Additionally or alternatively, the controller 2294 can be configured to receive inputs from sensors (e.g., sensors 180a-f; FIG. 2) on the device and control the device based on the received inputs. For example, the controller 2294 can determine any abnormalities of the operating device and automatically generate indications of the abnormalities and/or adjust the operating parameters of the device. Additionally or alternatively, the controller 2294 may utilize artificial intelligence and/or machine learning to adjust power and/or other control parameters, e.g., based on previous treatments used for the same user or a group of users.

The user interface 2296 can include a display, and/or an application or program that enables the user to utilize the device through a mobile device (e.g., a phone, tablet, watch, laptop, etc.) or other computing device. The user interface 1096 may include a plurality of pre-programmed thermal management procedures and/or enable the user to adjust cooling and heating parameters based on a desired application.

FIG. 22 is a flow diagram illustrating a method 2200 for treating a mammal (e.g., for pain, swelling, overheating, diminished blood perfusion, diminished nerve connectivity, and/or stroke) via a heat transfer device, in accordance with embodiments of the present technology. The method 2200 can comprise providing a heat transfer device (e.g., the device 100, 500, 700, 800, 900, 1000, 1100, 1200, 1300, 1400, 1500, 1600, 1700, 1800, 1900, 2000) (process portion 2202), and disposing the heat transfer device over a target area of a mammal (process portion 2204). Disposing the heat transfer device over the target area can comprise fastening the device over the target area, e.g., such that the device or flexible support unit of the device provides a compressive force on the target area and positions TECs of the device in thermal contact with the target area.

The method 2200 can further comprise initiating temperature control and/or an operating mode of the heat transfer device via a controller (e.g., the controller 2294; FIG. 22), thereby causing heat to transfer from the target area of the mammal to the heat transfer device or vice versa (process portion 2206). Initiating the operating mode can include initiating a cooling mode, a heating mode, or both a cooling mode and a heating mode. Initiating the temperature control can comprise providing a temperature for the TECs (e.g., the TECs 110; FIGS. 1A, 1B, 3-9) to operate at or a temperature at which the device is configured to heat or cool the target area within a predetermined time (e.g., 10 seconds, 20 seconds, 30 seconds, 40 seconds, 60 seconds, or 120 seconds). In some embodiments, the temperature can be set to be within a range of 40° C. to −20° C. (e.g., 35° C., 20° C., 0° C., −10° C., etc.).

V. Conclusion

It will be apparent to those having skill in the art that changes may be made to the details of the above-described embodiments without departing from the underlying principles of the present disclosure. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. The term "and/or" when used in reference to a list of two or more item is to be interpreted as including (a) any single item in the list, (b) all of the items in the list, or (c) any combination of the items in the list. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing numerical values used in the specification and claims, are to be understood as being modified in all instances by the term "about" or "approximately." The terms "about" or "approximately" when used in reference to a value are to be interpreted to mean within 10% of the stated value. Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples may be combined in any combination, and placed into a respective independent example. The other examples can be presented in a similar manner.

1. A wearable heat transfer device, comprising:
   thermoelectric components arranged in an array and spaced apart from each other, wherein individual thermoelectric components have a first side configured to be thermally coupled to a target area of a mammal and a second side opposite the first side;
   a heat transfer system having a condenser and an array of evaporators in which individual evaporators are thermally coupled to the second side of a corresponding one of the thermoelectric components and fluidically coupled to the condenser, wherein each of the evaporators has (a) a chamber with an inlet region and an outlet region and (b) microfeatures in the chamber spaced apart from each other such that, in operation, the microfeatures induce capillary forces to a working fluid that drive the working fluid from the inlet region of the chamber to the outlet region of the chamber; and
   a flexible support unit comprising a thermally conductive biocompatible flexible contact member coupled to the first sides of the thermoelectric components and extending at least between individual thermoelectric components, wherein the contact member is a heat spreader configured to enhance heat transfer from/to the target area of the mammal.

2. The device of any one of the clauses herein, wherein the flexible support unit is coupled to the thermoelectric components and configured such that, when the flexible support unit is attached to the mammal, the thermoelectric components are arranged to be adjacent the target area.

3. The device of any one of the clauses herein, wherein, when attached to the mammal, the flexible support unit is configured to exert a compressive force against the target area.

4. The device of any one of the clauses herein, wherein the heat transfer system is a two-phase heat transfer unit including the evaporators, and wherein the thermoelectric components and the two-phase heat transfer unit together have a height, measured along the direction of heat flow from the contact member through the thermoelectric component, of 1 mm to 25 mm.

5. The device of clause 4, further comprising a controller configured to (i) set the two-phase heat transfer unit to a first temperature of 40° C. to −20° C. at the second side of the thermoelectric components, and/or (ii) operate the thermoelectric components to heat the contact member to a second temperature of 20° C. to 40° C. in 1-10 seconds 6. The device of clause 4, wherein the two-phase heat transfer unit has a thickness measured in the direction of the heat flow from the thermoelectric component of 1 mm to 8 mm.

7. The device of any one of the clauses herein, wherein the microfeatures are spaced apart from each other by 10 microns to 1,000 microns.

8. The device of any one of the clauses herein, wherein the chambers include channels defined by walls of the microfeatures extending from the inlet region to the outlet region of the chamber.

9. The device of any one of the clauses herein, wherein the microfeatures are pins in the chamber.

10. The device of any one of the clauses herein, wherein the microfeatures are spaced apart from each other by 5 microns to 250 microns.

11. The device of any one of the clauses herein, wherein the flexible support unit comprises a flexible elastic material configured to be worn by the mammal such that the thermoelectric components are adjacent the target area, and wherein the thermoelectric components and the evaporators are supported either directly or indirectly by the flexible support unit.

12. The device of clause 11, further comprising a portable power source electrically coupled to the thermoelectric components such that the system is configured to be portably worn by the mammal.

13. The device of clause 12, wherein the power source is attached to the flexible support unit.

14. The device of clause 12, wherein the power source is separate from the flexible support unit and electrically coupled to the thermoelectric components by conductive lines.

15. The device of any one of the clauses herein, wherein the flexible support unit comprises an elastic wrap configured to be wrapped around the target area and straps with a fastener configured to retain the elastic wrap and exert a compressive force against the mammal.

16. The device of any one of the clauses herein, wherein the contact member comprises a metal sheet.

17. The device of any one of the clauses herein, wherein the contact member comprises (a) a metal sheet having a first side attached to the first sides of the thermoelectric components and a second side and (b) a non-metal contact material on the second side of the metal sheet.

18. The device of any one of the clauses herein, wherein the heat transfer unit includes a working fluid distribution passage in fluid communication with the array of evaporators and configured to supply the working fluid to the inlet region of the chamber of each of the evaporators.

19. The device of clause 18, further comprising a vapor collection passage in fluid communication with the array of evaporators and configured to collect vapor from the outlet region of the chamber of each of the evaporators.

20. The device of any one of the clauses herein, wherein the flexible support unit further comprises a backing material disposed over the contact member, wherein the thermoelectric components are embedded within the backing material.

21. The device of any one of the clauses herein, wherein the flexible support unit further comprises a backing material defining a plurality of pockets, wherein the thermoelectric components are disposed within the pockets of the backing material.

22. The device of any one of the clauses herein, further comprising a pressure adjustment member positioned radially outward of the evaporators, the pressure adjustment member being configured to increase and/or decrease the compressive force applied to the target tissue via the device.

23. The device of any one of the clauses herein, wherein the device is configured to treat an underlying condition including at least one of pain, swelling, overheating, diminished blood perfusion, diminished nerve connectivity, or stroke.

24. The device of any one of the clauses herein, wherein the device is configured to be worn around or on an arm, leg, back shoulder, head, or neck region of the mammal.

25. The device of any one of the clauses herein, wherein, in operation, the device is configured to cool the target area to a cooling depth of at least 1 mm, 2 mm, 3 mm, 4 mm, or 5 mm.

26. The device of any one of the clauses herein, wherein individual thermoelectric components have different orientations than other individual thermoelectric components.

27. The device of any one of the clauses herein, wherein individual evaporators have different orientations than other individual evaporators.

28. A wearable heat transfer device, comprising:
thermoelectric components arranged in an array and spaced apart from each other, wherein individual thermoelectric components have a first side configured to be thermally coupled to a target area of a mammal and a second side opposite the first side;
a heat transfer system including a heat exchanger and an array of fluid distribution networks in which individual fluid distribution networks are thermally coupled to the second side of a corresponding one of the thermoelectric components and fluidically coupled to the heat exchanger, wherein each of the fluid distribution networks has an inlet region, an outlet region, and microfeatures spaced apart from each other to at least partially define channels configured to receive a working fluid, wherein, in operation, the working fluid flows from the inlet region to the outlet region and absorbs heat from the microfeatures; and
a flexible support unit comprising a thermally conductive flexible contact member coupled to the first sides of the thermoelectric components and extending at least between individual thermoelectric components, wherein the contact member is a heat spreader configured to enhance heat transfer from the target area of the mammal.

29. The device of any one of the clauses herein, wherein:
the heat transfer system is a two-phase heat transfer system, the fluid distribution networks comprise evaporators each including a chamber that has the inlet region and the outlet region, the heat exchanger is a condenser, and in operation, the microfeatures induce capillary forces to the working fluid that drive the working fluid from the inlet region of the chamber to the outlet region of the chamber.

30. The device of clause 29, wherein the evaporators and the thermoelectric components together have a height, measured along the direction of heat flow from the contact member through the thermoelectric component, of 1 mm to 25 mm.

31. The device of clause 29, further comprising a controller configured to (i) set the second side of the thermoelectric components to a first temperature of 40° C. to −20° C., and/or (ii) operate the thermoelectric components to thermally treat the contact member to a second temperature of 40° C. to −20° C.

32. The device of clause 29, wherein individual evaporators have a thickness, measured in the direction of the heat flow from the thermoelectric component, of no more than 8 mm.

33. The device of clause 29, wherein the heat transfer system includes a working fluid distribution passage fluidically coupled to the array of evaporators and configured to supply the working fluid to the inlet region of the chamber of each of the evaporators.

34. The device of clause 33, further comprising a vapor collection passage fluidically coupled to the array of evaporators and configured to collect vapor from the outlet region of the chamber of each of the evaporators.

35. The device of any one of the clauses herein, wherein the channels are defined by walls of the microfeatures extending from the inlet region to the outlet region.

36. The device of any one of the clauses herein, wherein the inlet region of the fluid distribution network is positioned at an intermediate region of the fluid distribution network and the outlet region includes a first outlet at a first side of the fluid distribution network and a second outlet at a second side of the fluid distribution network opposite the first side.

37. The device of any one of the clauses herein, wherein the heat transfer system further comprises a pump fluidically coupled to the heat exchanger and the fluid distribution network, the pump being and configured to pump the working fluid throughout the heat transfer system.

38. The device of any one of the clauses herein, wherein the flexible support unit is coupled to the thermoelectric components and configured such that, when the flexible support unit is attached to the mammal, the thermoelectric components are arranged to be adjacent the target area.

39. The device of any one of the clauses herein, wherein, when attached to the mammal, the flexible support unit is configured to exert a compressive force against the target area.

40. The device of any one of the clauses herein, wherein the microfeatures are spaced apart from each other by 10 microns to 1,000 microns.

41. The device of any one of the clauses herein, wherein the microfeatures are pins in the chamber.

42. The device of any one of the clauses herein, wherein the microfeatures are spaced apart from each other by 5 microns to 250 microns.

43. The device of any one of the clauses herein, wherein the flexible support unit comprises a flexible elastic material configured to be worn by the mammal such that the thermoelectric components are adjacent the target area, and wherein the thermoelectric components and the evaporators are supported either directly or indirectly by the flexible support unit.

44. The device of any one of the clauses herein, further comprising a portable power source electrically coupled to the thermoelectric components such that the system is configured to be portably worn by the mammal.

45. The device of clause 44, wherein the power source is attached to the flexible support unit.

46. The device of clause 44, wherein the power source is separate from the flexible support unit and electrically coupled to the thermoelectric components by conductive lines.

47. The device of any one of the clauses herein, wherein the flexible support unit comprises an elastic wrap configured to be wrapped around the target area and straps with a fastener configured to retain the elastic wrap and exert a compressive force against the mammal.

48. The device of any one of the clauses herein, wherein the contact member comprises a metal sheet.

49. The device of any one of the clauses herein, wherein the contact member comprises (a) a metal sheet having a first side attached to the first sides of the thermoelectric components and a second side and (b) a non-metal contact material on the second side of the metal sheet.

50. The device of any one of the clauses herein, wherein the flexible support unit further comprises a backing material disposed over the contact member, wherein the thermoelectric components are embedded within the backing material.

51. The device of any one of the clauses herein, wherein the flexible support unit further comprises a backing material defining a plurality of pockets, wherein the thermoelectric components are disposed within the pockets of the backing material.

52. The device of any one of the clauses herein, further comprising a pressure adjustment member positioned radially outward of the evaporators, the pressure adjustment member being configured to increase and/or decrease the compressive force applied to the target tissue via the device.

53. The device of any one of the clauses herein, wherein the device is configured to treat an underlying condition including at least one of pain, swelling, overheating, diminished blood perfusion, diminished nerve connectivity, or stroke.

54. The device of any one of the clauses herein, wherein the device is configured to be worn around or on an arm, leg, back shoulder, head, or neck region of the mammal.

55. The device of any one of the clauses herein, wherein, in operation, the device is configured to cool the target area to a cooling depth of at least 1 mm, 2 mm, 3 mm, 4 mm, or 5 mm.

56. The device of any one of the clauses herein, wherein individual thermoelectric components have different orientations than other individual thermoelectric components.

57. The device of any one of the clauses herein, wherein individual fluid distribution networks have different orientations than other individual fluid distribution networks.

58. A device for treating pain and/or swelling in a mammal, comprising:

thermoelectric components arranged in an array and spaced apart from each other, wherein individual thermoelectric components have a first side configured to be thermally coupled to a target area of a mammal and a second side opposite the first side;

a heat transfer system having a condenser and an array of evaporators in which individual evaporators are thermally coupled to the second side of a corresponding one of the thermoelectric components and fluidically coupled to the condenser, wherein each of the evaporators has (a) a chamber with an inlet region and an outlet region and (b) microfeatures in the chamber spaced apart from each other such that, in operation, the microfeatures induce capillary forces to a working fluid that drive the working fluid from the inlet region of the chamber to the outlet region of the chamber;
    a flexible support unit coupled to the thermoelectric components and configured such that, when attached to the mammal, the thermoelectric components are arranged to be adjacent to the target tissue, wherein the flexible support unit is configured to exert a compressive force against the target area;
    a temperature sensor positioned relative to the thermoelectric components to measure a temperature associated with the target area; and
    a controller coupled to the thermoelectric components, wherein the controller is configured to operate the thermoelectric components and the heat transfer system such that the heat transfer system cools the second side of the thermoelectric components to a first temperature and the thermoelectric components changes the temperature of the target area to a second temperature within 0.5-20 seconds, and wherein the second temperature is +/−40° C. to −20° C. of the first temperature.

59. The device of any one of the clauses herein, wherein the flexible support unit comprises a thermally conductive biocompatible flexible contact member coupled to the first sides of the thermoelectric components and extending at least between individual thermoelectric components, wherein the contact member is a heat spreader configured to enhance heat transfer from/to the target area of the mammal.

60. The device of any one of the clauses herein, wherein the contact member comprises a metal sheet.

61. The device of any one of the clauses herein, wherein, when attached to the mammal, the flexible support unit is configured to exert a compressive force against the target area.

62. The device of any one of the clauses herein, wherein the heat transfer system is a two-phase heat transfer unit including the evaporators, and wherein the thermoelectric components and the two-phase heat transfer unit together have a height, measured along the direction of heat flow from the contact member through the thermoelectric component, of 1 mm to 25 mm.

63. The device of clause 62, further comprising a controller configured to (i) set the two-phase heat transfer unit to a first temperature of 40° C. to −20° C. at the second side of the thermoelectric components, and/or (ii) operate the thermoelectric components to heat the contact member to a second temperature of 20° C. to 40° C. in 1-10 seconds 64. The device of clause 62, wherein the two-phase heat transfer unit has a thickness measured in the direction of the heat flow from the thermoelectric component of 1 mm to 8 mm.

65. The device of any one of the clauses herein, wherein the chambers include channels defined by walls of the microfeatures extending from the inlet region to the outlet region of the chamber.

66. The device of any one of the clauses herein, wherein the microfeatures are pins in the chamber.

67. The device of any one of the clauses herein, wherein the microfeatures are spaced apart from each other by 5 microns to 250 microns.

68. The device of any one of the clauses herein, wherein the flexible support unit comprises a flexible elastic material configured to be worn by the mammal such that the thermoelectric components and the evaporators are supported either directly or indirectly by the flexible support unit.

69. The device of any one of the clauses herein, wherein the flexible support unit comprises an elastic wrap configured to be wrapped around the target area and straps with a fastener configured to retain the elastic wrap and exert a compressive force against the mammal.

70. A method for transferring heat to and/or from a mammal, comprising:
    providing a heat transfer device including
        thermoelectric components each having a first side and a second side opposite the first side;
        an array of evaporators each being thermally coupled to the second side of a corresponding one of the thermoelectric components and fluidically coupled to a condenser, wherein, in operation, a working fluid disposed within the evaporators transitions from a liquid phase to a vapor phase to enable heat transfer from the corresponding one of the thermoelectric components; and
        a flexible support unit coupled to the first sides of the thermoelectric components and extending at least between individual thermoelectric components, the flexible support unit being a heat spreader configured to enhance heat transfer from the mammal;
    disposing the heat transfer device over a target area of the mammal such that (i) the flexible support unit is disposed at least partially around the target area and exerts a compressive force on the target area, and (ii) the thermoelectric components of the heat transfer device are thermally coupled to the target area;
    initiating, via a controller operatively coupled to the heat transfer device, an operating mode of the heat transfer device, thereby causing heat to transfer from the target area of the mammal to the heat transfer device and cool the target area.

71. The method of any one of the clauses herein, wherein the flexible support unit comprises a thermally conductive flexible member coupled to the first sides of the thermoelectric components and extending at least between individual thermoelectric components, wherein the thermoelectric components are thermally coupled to the target area via the contact member.

72. The method of any one of the clauses herein, wherein disposing the heat transfer device over the target area comprises disposing the contact member directly against the mammal.

73. The method of any one of the clauses herein, wherein initiating the operating mode comprises setting the heat transfer unit to a temperature of −20° C. to 40° C.

74. The method of any one of the clauses herein, wherein initiating the operating mode causes the device to cool the target area to a temperature of −20° C. to 40 C in 1-10 second.

75. The method of clause 74, wherein the operating mode is a first operating mode, the method further comprising initiating a second operating mode during which heat is provided to the target area via the heat transfer device.

76. The method of any one of the clauses herein, wherein the flexible support unit comprises an elastic material configured to be worn by the mammal such that the thermoelectric components are adjacent the target area, and wherein the thermoelectric components and the evaporators are supported either directly or indirectly by the flexible support unit.

77. The method of any one of the clauses herein, wherein the flexible support unit comprises (a) a metal sheet having a first side attached to the first sides of the thermoelectric components and a second side and (b) a non-metal contact material on the second side of the metal sheet.

78. The method of any one of the clauses herein, wherein each of the evaporators includes (a) a chamber with an inlet region and an outlet region and (b) microfeatures in the chamber spaced apart from each other, and wherein initiating the operating causes the microfeatures to induce capillary forces to the working fluid that drive the working fluid in a liquid phase at the inlet region of chamber to a vapor phase at the outlet region of the chamber.

79. The method of any one of the clauses herein, wherein the target area comprises a region of an arm, leg, lower body, or upper body of the mammal, and wherein disposing the heat transfer device over the target area comprises disposing the heat transfer device such that the flexible support unit is wrapped entirely around the target area.

80. A wearable heat transfer system configured to be disposed at an ocular region of a mammal, the system comprising:
    a thermally conductive member in thermal contact with a target area of the ocular region;
    thermoelectric components spaced apart from one another and disposed over the thermally conductive member, individual thermoelectric components having a first side thermally coupled to the thermally conductive member and a second side opposite the first side; and
    a heat transfer unit disposed over the thermally conductive member, such that the thermoelectric components are between the thermally conductive member and at least a portion of the heat transfer unit, the heat transfer unit comprising fluid distribution networks each disposed over a corresponding one of the thermoelectric components and a heat exchanger fluidically coupled to the fluid distribution networks, the heat transfer system being configured to remove heat from the thermoelectric components.

81. The heat transfer system of any one of the clauses herein, wherein the thermally conductive member is configured to be disposed directly on an under-eye region of the mammal.

82. The heat transfer system of any one of the clauses herein, wherein the thermally conductive member is a plate comprising metal, metallic alloy, polymer, and/or silicone.

83. The heat transfer system of any one of the clauses herein, wherein the fluid distribution networks each comprise an evaporator, and wherein each of the evaporators has (a) a chamber with an inlet region and an outlet region and (b) microfeatures in the chamber spaced apart from each other such that, in operation, the microfeatures induce capillary forces to a working fluid that drive the working fluid from the inlet region of the chamber to the outlet region of the chamber.

84. The heat transfer system of any one of the clauses herein, wherein the thermoelectric components are each connected to a portable power source and a controller, such that individual thermoelectric components can be set to operate at a desired temperature between 10° C. to 0° C.

85. The heat transfer device of any one of the clauses herein, where the device is configured to treat at least one of under eye puffiness, under eye bags, dark circles, or eye hollows.

86. The heat transfer system of any one of the clauses herein, wherein at least one of the thermally conductive member or the heat transfer unit has a crescent shape.

87. The heat transfer system of any one of the clauses herein, wherein an upper surface and/or lower surface of the thermally conductive member has a concave shape.

88. The heat transfer system of any one of the clauses herein, further comprising a sensor configured to measure a temperature of at least one of the TECs or the target area.

89. The heat transfer system of any one of the clauses herein, wherein the thermally conductive member, thermoelectric components, and heat transfer unit comprise a heat transfer device, the heat transfer system further comprising an ocular device including a frame configured to be worn by the mammal and attached to the heat transfer device, wherein when the frame is worn by the mammal the heat transfer device is positioned at the target area.

90. The heat transfer system of any one of the clauses herein, wherein:
    the fluid distribution networks each comprise an evaporator, and each of the evaporators has (a) a chamber with an inlet region and an outlet region and (b) microfeatures in the chamber spaced apart from each other such that, in operation, the microfeatures induce capillary forces to a working fluid that drive the working fluid from the inlet region of the chamber to the outlet region of the chamber.
    the heat transfer unit includes (i) a liquid distribution passage in fluid communication with the evaporators and configured to supply the liquid working fluid to the chamber of each of the evaporators, and (ii) a vapor collection passage in fluid communication with the evaporators and configured to collect vapor working fluid from the chamber of each of the evaporators;
    wherein the heat transfer system further comprising an ocular device including a frame configured to be worn by the mammal, at least part of the liquid distribution passage or vapor collection passage being disposed on or within the frame.

We claim:
1. A heat transfer device, comprising:
    thermoelectric components arranged in an array and spaced apart from each other, wherein individual thermoelectric components have a first side configured to be thermally coupled to a target area of a mammal and a second side opposite the first side;
    a heat transfer system comprising—
        a heat exchanger,
        a common inlet fluid distribution passage fluidically coupled to the heat exchanger,
        a common outlet fluid distribution passage fluidically coupled to the heat exchanger, and
        fluid distribution networks fluidically coupled in parallel to the common inlet fluid distribution passage and the common outlet fluid distribution passage, wherein—
            each of the fluid distribution networks is thermally coupled to the second side of a corresponding one of the thermoelectric components,
            each of the fluid distribution networks includes an inlet region fluidically coupled to the common inlet fluid distribution passage, an outlet region fluidically coupled to the common outlet fluid distribution passage, and microfeatures spaced apart from each other along a first axis to at least partially define channels configured to receive a working fluid, and in operation, the working fluid flows from the inlet region to the outlet region and absorbs heat from the microfeatures, wherein the microfeatures are spaced apart from corresponding thermoelectric components along a second axis, perpendicular to the first axis, by a first distance and one of the common inlet fluid distribution passage or the common outlet fluid distribution passage is spaced apart from the corresponding thermoelectric components along the second axis by a second distance greater than the first distance, and wherein a distance between the first side of the individual thermoelectric components and an outermost surface of one of the common inlet fluid distribution passage or the common outlet fluid distribution passage is no more than 30 millimeters; and a flexible support unit coupled to the first side of the thermoelectric components such that when the flexible support unit is attached to the mammal the thermoelectric components are arranged to be adjacent to the target area.

2. The device of claim 1, wherein the common inlet fluid distribution passage and the common outlet fluid distribution passage are spaced apart from the corresponding thermoelectric components along the second axis by at least the second distance.

3. The device of claim 1, wherein the common inlet fluid distribution passage is spaced apart from the corresponding thermoelectric components by the second distance and the common outlet fluid distribution passage is spaced apart from the corresponding thermoelectric components by a third distance greater than the second distance.

4. The device of claim 1, further comprising a temperature sensor positioned to measure a temperature associated with the target area.

5. The device of claim 4, further comprising a controller coupled to the thermoelectric components and the temperature sensor, wherein the controller is configured to operate the thermoelectric components based at least in part on the temperature measured via the temperature sensor.

6. The device of claim 1, further comprising a controller coupled to the thermoelectric components, wherein the controller is configured to operate the thermoelectric components such that the first side of the thermoelectric components is set to a first temperature, and the heat transfer system cools the second side of the thermoelectric components to a second temperature greater than the first temperature.

7. The device of claim 6, wherein the thermoelectric components include a first thermoelectric component and a second thermoelectric component, and wherein the controller is configured to individually control the first thermoelectric component and the second thermoelectric component to have unique temperatures.

8. The device of claim 1, wherein the flexible support unit comprises a thermally conductive flexible member coupled to the first sides of the thermoelectric components and extending at least between individual thermoelectric components, wherein the thermoelectric components are thermally coupled to the target area via the flexible member.

9. The device of claim 1, wherein, when the flexible support unit is attached to the mammal, the flexible support unit exerts a compressive force against the target area.

10. The device of claim 1, wherein a distance between a first face of the individual thermoelectric components adjacent the target area and an outermost surface of the heat transfer system is less than 15 millimeters.

11. The device of claim 1, wherein the inlet regions of each of the fluid distribution networks are fluidically coupled to the common inlet fluid distribution passage at different areas of the common inlet fluid distribution passage.

12. A wearable heat transfer device, comprising:
thermoelectric components arranged in an array and spaced apart from each other, wherein individual thermoelectric components have a first side configured to be thermally coupled to a target area of a mammal and a second side opposite the first side;

a heat transfer system comprising—
a heat exchanger,
a common inlet fluid distribution passage fluidically coupled to the heat exchanger,
a common outlet fluid distribution passage fluidically coupled to the heat exchanger, and
an array of fluid distribution networks fluidically coupled in parallel to the common inlet and outlet fluid distribution passages, wherein each of the fluid distribution networks (i) is thermally coupled to the second side of a corresponding one of the thermoelectric components, and (ii) includes an inlet region fluidically coupled to the common inlet fluid distribution passage, and an outlet region fluidically coupled to the common outlet fluid distribution passage; and a flexible support unit comprising a thermally conductive flexible contact member coupled to the first sides of at least some of the thermoelectric components, wherein the contact member is configured to enhance heat transfer from and/or to the target area of the mammal, and wherein, along an axis extending away from the target area when the device is worn by the mammal, the flexible support unit is inward of the individual thermoelectric components, the individual thermoelectric components are inward of the corresponding fluid distribution networks, and the fluid distribution networks are inward of at least one of the common inlet fluid distribution passage or the common outlet fluid distribution passage, wherein a distance between the first side of the individual thermoelectric components and an outermost surface of one of the common inlet fluid distribution passage or the common outlet fluid distribution passage is no more than 30 millimeters.

13. The device of claim 12, wherein the fluid distribution networks are inward of the common inlet fluid distribution passage and the common outlet fluid distribution passage along the axis.

14. The device of claim 12, wherein the common inlet fluid distribution passage is inward of the common outlet fluid distribution passage along the axis.

15. The device of claim 12, wherein the contact member is coupled to the first sides of the thermoelectric components and extends between individual thermoelectric components, such that the thermoelectric components are thermally coupled to the target area via the contact member.

16. The device of claim 12 wherein, when the flexible support unit is attached to the mammal, the flexible support unit exerts a compressive force against the target area.

17. The device of claim 12, wherein:
the axis is a first axis,
each of the fluid distribution networks includes microfeatures spaced apart from each other along a second axis, normal to the first axis, to at least partially define elongate channels configured to receive a working fluid, and in operation, the working fluid flows in a lateral direction from the inlet region to the outlet region between adjacent elongate channels and absorbs heat from the microfeatures.

18. The device of claim 17, wherein a distance between adjacent microfeatures is no more than 1000 microns.

19. The device of claim 12, wherein a distance between a first face of the individual thermoelectric components adjacent the target area and the outermost surface is less than 15 millimeters.

20. A method for transferring heat from a mammal to a heat transfer device, the method comprising:
providing a wearable heat transfer device comprising—
thermoelectric components arranged in an array and spaced apart from each other, wherein individual thermoelectric components have a first side configured to be thermally coupled to a target area of a mammal and a second side opposite the first side;
a heat transfer system comprising—
a heat exchanger,
a common inlet fluid distribution passage fluidically coupled to the heat exchanger,
a common outlet fluid distribution passage fluidically coupled to the heat exchanger, and
an array of fluid distribution networks fluidically coupled in parallel to the common inlet fluid distribution passage and the common outlet fluid distribution passage, wherein—
each of the fluid distribution networks is thermally coupled to the second side of a corresponding one of the thermoelectric components,
each of the fluid distribution networks includes an inlet region fluidically coupled to the common inlet fluid distribution passage, and an outlet region fluidically coupled to the common outlet fluid distribution passage, and
in operation, a working fluid flows from the inlet region to the outlet region and absorbs heat from the fluid distribution network; and
a flexible support unit coupled to the thermoelectric components,
wherein a distance between the first side of the individual thermoelectric components and an outermost surface of one of the common inlet fluid distribution passage or the common outlet fluid distribution passage is no more than 30 millimeters;
disposing the heat transfer device over a target area of the mammal such that (i) the flexible support unit is disposed at least partially around the target area and exerts a compressive force on the target area, (ii) the thermoelectric components of the heat transfer device are thermally coupled to the target area, and (iii) along an axis extending away from the target area, the flexible support unit is inward of the individual thermoelectric components, the individual thermoelectric components are inward of the corresponding fluid distribution networks, and the fluid distribution networks are inward of at least one of the common inlet fluid distribution passage or the common outlet fluid distribution passage; and
initiating, via a controller operatively coupled to the thermoelectric components, temperature control of the heat transfer device, thereby causing heat to transfer from the target area of the mammal to the heat transfer device.

21. The method of claim 20, wherein the fluid distribution networks are inward of the common inlet fluid distribution passage and the common outlet fluid distribution passage along the axis.

22. The method of claim 20, wherein the common inlet fluid distribution passage is inward of the common outlet fluid distribution passage along the axis.

23. The method of claim 20, wherein the thermoelectric components include a first thermoelectric component and a second thermoelectric component, and wherein initiating temperature control of the heat transfer device comprises individually controlling each of the first thermoelectric component and the second thermoelectric component such that the first thermoelectric component is set to a first temperature and the second thermoelectric component is set to a second temperature different than the first temperature.

24. The method of claim 20, wherein the heat transfer device further comprises a temperature sensor, the method further comprising:
measuring, via the temperature sensor, a temperature associated with the target area; and
controlling the temperature of the thermoelectric components based on the measured temperature.

25. The method of claim 20, wherein disposing the heat transfer device over the target area comprises disposing the contact member directly against the mammal.

26. The method of claim 20, wherein initiating the temperature control comprises setting the thermoelectric components to a temperature within a range of −20° C. to 20° C. to thermally treat the target area.

27. The method of claim 20, wherein initiating the temperature control comprises initiating a first operating mode, the method further comprising initiating a second operating mode during which heat is provided to the target area via the heat transfer device.

28. A heat transfer device, comprising:
a first thermoelectric component including a first side configured to be thermally coupled to a target area of a mammal and a second side opposite the first side;
a second thermoelectric component spaced apart from the first thermoelectric component along a first axis, the second thermoelectric component including a first side configured to be thermally coupled to the target area of the mammal and a second side opposite the first side; and
a heat transfer system comprising—
a heat exchanger,
a common inlet fluid distribution passage fluidically coupled to the heat exchanger,
a common outlet fluid distribution passage fluidically coupled to the heat exchanger,
a first fluid distribution network thermally coupled to the second side of the first thermoelectric component, first fluid distribution network being fluidically coupled to the common inlet fluid distribution passage via a first inlet region and to the common outlet fluid distribution passage via a first outlet region, and
a second fluid distribution network thermally coupled to the second side of the second thermoelectric component, the second fluid distribution network being fluidically coupled to the common inlet fluid distribution passage via a second inlet region and to the common outlet fluid distribution passage via a second outlet region, wherein—
the first fluid distribution network is spaced apart from the first thermoelectric component along a second axis, perpendicular to the first axis, by a first distance,
at least one of the common inlet fluid distribution passage or the common outlet fluid distribution passage is spaced apart from the first thermoelectric component along the second axis by a second distance greater than the first distance, and
wherein a distance between the first side of the first thermoelectric component and an outermost surface of the common inlet fluid distribution passage or the common outlet fluid distribution passage is no more than 30 millimeters.

29. The device of claim 28, wherein the first inlet region of the first fluid distribution network is fluidly coupled to the common inlet fluid distribution passage at a first point and the second inlet region of the second fluid distribution network is fluidly coupled to the common inlet fluid distribution passage at a second point different than the first point.

30. The device of claim 29, wherein the common inlet fluid distribution passage is fluidically coupled to the heat exchanger at a third point upstream of the first point and the second point.

* * * * *